United States Patent
Rajguru et al.

(10) Patent No.: US 10,271,987 B2
(45) Date of Patent: Apr. 30, 2019

(54) LOCALIZED THERAPEUTIC HYPOTHERMIA SYSTEM, DEVICE, AND METHOD

(71) Applicants: Lucent Medical Systems, Inc., Kirkland, WA (US); University of Miami, Miami, FL (US)

(72) Inventors: Suhrud Rajguru, Coral Gables, FL (US); Efrem Ari Roberson, McLean, VA (US); Curtis S. King, Kirkland, WA (US); Thomas J. Balkany, Silverthorne, CO (US)

(73) Assignees: Lucent Medical Systems, Inc., Kirkland, WA (US); University of Miami, Miami, FL (US)

( * ) Notice: Subject to any disclaimer, the term of this patent is extended or adjusted under 35 U.S.C. 154(b) by 739 days.

(21) Appl. No.: 14/626,081

(22) Filed: Feb. 19, 2015

(65) Prior Publication Data
US 2015/0238354 A1 Aug. 27, 2015

Related U.S. Application Data

(60) Provisional application No. 61/943,734, filed on Feb. 24, 2014.

(51) Int. Cl.
*A61F 7/12* (2006.01)
*A61F 7/00* (2006.01)

(52) U.S. Cl.
CPC ........ *A61F 7/12* (2013.01); *A61F 2007/0005* (2013.01); *A61F 2007/0056* (2013.01);
(Continued)

(58) Field of Classification Search
CPC ................ A61F 7/12; A61F 2007/0005; A61F 2007/0056; A61F 2007/0076
See application file for complete search history.

(56) References Cited

U.S. PATENT DOCUMENTS 6,514,245 B1 * 2/2003 Williams ............... A61B 18/02
128/898
6,673,098 B1 * 1/2004 Machold ................. A61F 7/123
607/104

(Continued)

FOREIGN PATENT DOCUMENTS

WO 2010/091364 A1 8/2010
WO 2013/164820 A1 11/2013

OTHER PUBLICATIONS

Yasumitsu Ohkoshi, "The Effect of Cryotherapy on Intraarticular Temperature and Postoperative Care After Anterior Cruciate Ligament Reconstruction," 1999, vol. 27, pp. 357-362.*

(Continued)

*Primary Examiner* — Joseph Stoklosa
*Assistant Examiner* — Adam Avigan
(74) *Attorney, Agent, or Firm* — Seed IP Law Group LLP

(57) ABSTRACT

Therapeutic application of mild to moderate hypothermia in a medical procedure has been found to provide benefits to patients. For example, application of mild hypothermia in the auditory pathway can prevent functional hearing loss post cochlear implant surgery. Devices have been conceived and reduced to practice that apply localized cooling to a small area such as the basal or middle turn of the cochlea. The devices include a cooling tip with at least one thermoconductive surface. A heat-transporting fluid is circulated through the cooling tip. After absorbing heat, the heat-transporting fluid may be controllably cooled with a thermoelectric cooling device.

21 Claims, 18 Drawing Sheets

(52) U.S. Cl.
CPC ............... *A61F 2007/0076* (2013.01); *A61F 2007/0095* (2013.01)

(56) References Cited

U.S. PATENT DOCUMENTS

| | | | | |
|---|---|---|---|---|
| 7,244,253 | B2* | 7/2007 | Neev | A61B 18/203 362/572 |
| 7,591,814 | B2 | 9/2009 | Santoianni et al. | |
| 2003/0028229 | A1 | 2/2003 | Rothman | |
| 2004/0210281 | A1* | 10/2004 | Dzeng | A61F 7/123 607/96 |
| 2011/0040361 | A1* | 2/2011 | Levy | A61F 7/00 607/114 |
| 2011/0098719 | A1* | 4/2011 | Llinas | A61N 1/0541 606/129 |
| 2011/0245902 | A1* | 10/2011 | Katz | A61F 7/10 607/113 |
| 2011/0276115 | A1* | 11/2011 | Merrill | A61F 7/12 607/106 |
| 2013/0073015 | A1* | 3/2013 | Rozenberg | A61F 7/0085 607/106 |
| 2013/0172966 | A1* | 7/2013 | Arad | A61F 7/0085 607/105 |
| 2013/0218160 | A1* | 8/2013 | Bjorn | A61B 17/1695 606/80 |

OTHER PUBLICATIONS

Brown et al., "Cryoprobe-induced apical lesions in the chinchilla. I. Morphological effects of lesioning paramaters," *Hearing Research* 26:301-309, 1987.

Eshraghi et al., "Cochlear Implantation Trauma and Noise-Induced Hearing Loss: Apoptosis and Therapeutic Strategies," *The Anatomical Record Part A* 288A:473-481, 2006.

International Search Report and Written Opinion, dated May 19, 2015, for corresponding International Application No. PCT/US2015/016602, 16 pages.

Prosen et al., "Apical hair cells and hearing," *Hearing Research* 44:179-194, 1990.

\* cited by examiner

LOCALIZED THERAPEUTIC HYPOTHERMIA SYSTEM, DEVICE, AND METHOD

CROSS-REFERENCE(S) TO RELATED APPLICATION(S)

This application claims the benefit under 35 U.S.C. § 119(e) of U.S. Provisional Patent Application No. 61/943,734 filed Feb. 24, 2014, which application is hereby incorporated by reference in its entirety.

BACKGROUND

Technical Field

The present disclosure generally relates to a medical device used to provide localized therapeutic hypothermia at a small situs. More particularly, but not exclusively, the present disclosure relates to a device that reduces temperature in the area around a cochlea during a medical procedure to implant an auditory prostheses.

Description of the Related Art

In many medical procedures, a medical practitioner accesses internal loci of a patient. In some cases, the medical practitioner accesses the internal loci for diagnostic purposes. In other cases, the practitioner accesses the loci to provide treatment. In still other cases, different therapy is provided.

FIG. 1 illustrates the anatomy of a human ear. In FIG. 1, the cartilage and fleshy tissue of the right, outer ear 12 is shown. The external auditory canal 14 provides a pathway for sound to enter the middle ear. The external auditory canal 14 passes through the external and internal acoustic meatus of the skull, which forms a space near the floor of the skull 16 and the upper bone 18 of the mandible. The middle ear includes the tympanic membrane 20, which is more readily known as the eardrum, and the tympanic cavity 22. Sound waves pass through the ear drum and into the tympanic cavity 22. The middle ear transfers the sound waves to the fluid of the cochlea 30. To help orient the anatomical features illustrated in FIG. 1, the Eustachian tube 24, semicircular canals 26, vestibular nerve 28, and cochlear nerve 32 are also shown.

The rolled up spiral of the cochlea 30 looks like a snail shell ("cochlea" is a Greek word for snail) and functions to transform the vibrations of the cochlear liquids and associated structures into a neural signal. The neural signal is sensed by the cochlear nerve 32 and passed into the auditory structures of the brain.

Along the spiral of the cochlea 30, various frequencies are noted in FIG. 1. An area at the entrance (base) of the cochlea 30 is indicated at 16 kilohertz (kHz); a second area at 1 kHz and a third area at 0.5 kHz are also identified. Generally speaking, higher frequencies (e.g., 20 kHz to about 1.5 kHz) are sensed at the base of the cochlea 30, mid-range frequencies (e.g., 1.5 kHz to about 600 Hz) are sensed in the middle of the cochlea 30, and lower frequencies (e.g., 600 Hz to about 200 Hz) are sensed toward the tip of the cochlea 30.

FIGS. 2A-2C illustrates three cutaway portions of a cochlea 30. In FIG. 2A, a terminal end portion of the cochlea 30 is shown along with a cochlear duct 34. Long cilia 36 (i.e., hair cells) are shown. The long, flexible hair cells are formed to tune to the lower frequencies sensed at the tip of the cochlea 30. Mid-range frequencies are sensed by the medium cilia 38 shown in FIG. 2B, and high frequencies are sensed by the short cilia 40 shown in FIG. 2C.

When parts of the ear that transmit sound to the cochlear nerve 32 are damaged, the person will experience partial or total hearing loss. In the case of mild or moderate hearing loss, the person often benefits from a hearing aid, which is an amplifier worn in the external auditory canal 14. The hearing aid amplifies sound so that a more intense sound wave is passed into the middle ear. In cases where the sound reception mechanism in the cochlea 30 is more severely damaged however, the hearing aid is of little help. One alternative to a hearing aid for a select group of patients is cochlear implant.

FIG. 3 illustrates a cochlear electrode array 46 implanted in a human cochlea 30. The cochlear electrode array 46 bypasses the damaged part of the ear and transmits sound signals directly to the cochlear nerve. Signals provided at the cochlear electrode array 46 originate at a cochlear transmitter 42 and pass down a cochlear probe 44. The cochlear probe passes through a hole in the skull. When the device is operating, external sound is picked up by a microphone (not shown) worn behind the patient's ear. The sound is electronically processed and passed to a stimulator/transmitter. Sequences of electrical pulses are passed down the cochlear probe 44 to the cochlear electrode array. The electrodes of the array stimulate the cochlear nerve, thereby bypassing the damaged portions of the middle and inner ear. Each electrode in the array is tuned to a particular frequency range so as to mimic the frequency separation and identification mechanism of a healthy ear.

BRIEF SUMMARY

In accordance with some embodiments described herein, therapeutic application of mild to moderate hypothermia in the auditory pathway has been found to prevent functional hearing loss, for example, post cochlear implant surgery. This may be particularly useful to protect residual hearing in patients who undergo medical procedures to implant hybrid electro-acoustic stimulation devices. This may also be useful to patients who have suffered other types of middle and inner ear distress. Devices have been conceived and reduced to practice that fit proximal to the middle turn of the cochlea. Other devices have been conceived and reduced to practice that fit within the external auditory canal or at other middle and inner ear sites. The devices provide localized, therapeutic mild hypothermia. The devices are effective to reduce or prevent functional loss correlated with middle and inner ear distress such as surgical trauma.

In a first embodiment, a medical device to locally cool a cochlear region includes a thermally conductive cooling tip and a multiport catheter coupled to the thermally conductive cooling tip. The multiport catheter has a first lumen and a second lumen. The first lumen is arranged to pass a fluid in a first direction toward the thermally conductive cooling tip, and the second lumen is arranged to pass the fluid in a second direction away from the thermally conductive cooling tip. A pump has an output port coupled to the first lumen and an input port coupled to the second lumen. The pump is configured to move the fluid. A thermoelectric cooling system has a cooling side and an opposite side, and the cooling side is assembled in proximity to a portion of the multiport catheter.

The medical device of the first embodiment may optionally include a control module configured to control at least one parameter, electric current for example, of the thermoelectric cooling system. The medical device of the first embodiment may optionally include one or more temperature responsive elements coupled to the control module, and may also optionally include a user interface coupled to the control module. In such embodiments, the user interface is arranged to accept at least one input parameter associated with a temperature of the thermally conductive cooling tip, and the user interface is arranged to present at least one status output. A biocompatibility agent is sometimes arranged on an outer surface of the thermally conductive cooling tip, which may be formed using at least one metal. Another optional feature of the first embodiment is component-based construction. That is, in some cases, the multiport catheter and the thermally conductive cooling tip can be removed from the medical device for sterilization.

In another embodiment, a medical device is formed with a multiport catheter, a thermally conductive cooling tip, and a sealing structure. The thermally conductive cooling tip has a body with a substantially cylindrical shape and formed of a thermally conductive material. The body forms a closed cavity having a first orifice coupled to a first lumen of the multiport catheter and a second orifice coupled to a second lumen of the multiport catheter. The sealing structure joins the multiport catheter to the thermally conductive cooling tip.

The medical device of the second embodiment may optionally include a temperature responsive element integrated with the thermally conductive cooling tip, and the multiport catheter may include first and second lumens; a first lumen arranged to pass a fluorocarbon into the thermally conductive cooling tip and a second lumen arranged to pass the fluorocarbon out from the thermally conductive cooling tip. In some embodiments, the thermally conductive cooling tip is shaped to mate with at least one structure of a vestibular system so as to facilitate more efficient temperature transfer. In other cases, the medical device of the second embodiment also couples a thermoelectric cooling system to the multiport catheter. Sometimes, to facilitate patient comfort or for other reasons, the outer surface of the thermally conductive cooling tip may include a biocompatible material.

Another embodiment executes acts to provide localized therapeutic hypothermia. A first act places a cooling tip, which may have a cavity of less than 60 mm$^3$, in proximity to a biological structure to be cooled, wherein the cooling tip has thermo-conductive properties. A second act pumps a heat-transporting fluid into and out from an internal cavity of the cooling tip, and a third act removes heat from the heat-transporting fluid with a thermoelectric cooling device. The thermoelectric cooling device is controlled to achieve a determined temperature in an area proximate the cooling tip. The embodiment includes other optional acts too such as an act to perform a medical procedure on the biological structure that causes some trauma to the biological structure. In these cases, the cooling tip is placed in proximity to the biological structure to be cooled between 15 and 30 minutes before the biological structure is traumatized. Along these lines, another optional act may also place the cooling tip in proximity to the biological structure between 15 and 30 minutes after the structure is traumatized. In some cases, the medical procedure includes the implantation of a cochlear device. Other medical procedures are also contemplated. In some cases, such as when a patient is in proximity to very loud noise, an area of biological material can be damaged. In these cases, another optional act of the third embodiment includes placing the cooling tip in proximity to the biological structure within 48 hours after the biological structure is traumatized.

These features with other objects and advantages which will become subsequently apparent reside in the details of construction and operation as more fully described hereafter and claimed, reference being had to the accompanying drawings forming a part hereof.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

Sounds can be harmful when they are too loud or above a safe level, even for a brief time. Long-lasting loud sounds can be further harmful and cause significant damage. At unsafe levels, sounds may damage sensitive structures in the inner ear and cause noise-induced hearing loss (NIHL).

NIHL may be caused by a one-time exposure to an intense "impulse" sound, such as an explosion or blast. Repeated impulse sounds such as gun blasts (e.g., from target shooting or hunting), factory work, construction work, and the like may also cause NIHL and so may continuous exposure to loud sounds over an extended period of time, such as noise generated in a music concert or machine shop and listening to music at high volume through headphones. NIHL may be immediate or may occur over a period of time, and it is recognized that as sound volume increases, the shorter the amount of time it takes for NIHL to happen.

NIHL may lead to permanent loss of residual hearing and other detrimental effects such as tinnitus, which is a ringing or buzzing in one or both ears. Other problems attributable to NIHL include balance deficits, which occur when vestibular otolith organs, particularly the biomechanically susceptible saccule, are injured.

NIHL can be temporary or permanent, and it can affect one ear or both ears. It is estimated that about 15 percent of people between the ages of 20 and 69 have some degree of hearing loss caused by exposure to noise. Young people engaged in modern culture may be particularly affected through their use of over-the-ear and in-ear audio headphones to loudly play their music of choice. In fact, the Centers for Disease Control and Prevention in 2010 reported as many as 16 percent of young people aged 12 to 19 have reported some hearing loss generally attributed to loud noise.

A cochlear implant does not always provide a whole benefit. In many cases, the benefits provided by a cochlear implant outweigh any negative effects. Nevertheless, the negative effects may create unintended consequences that negatively affect patient outcomes.

Figure 1:
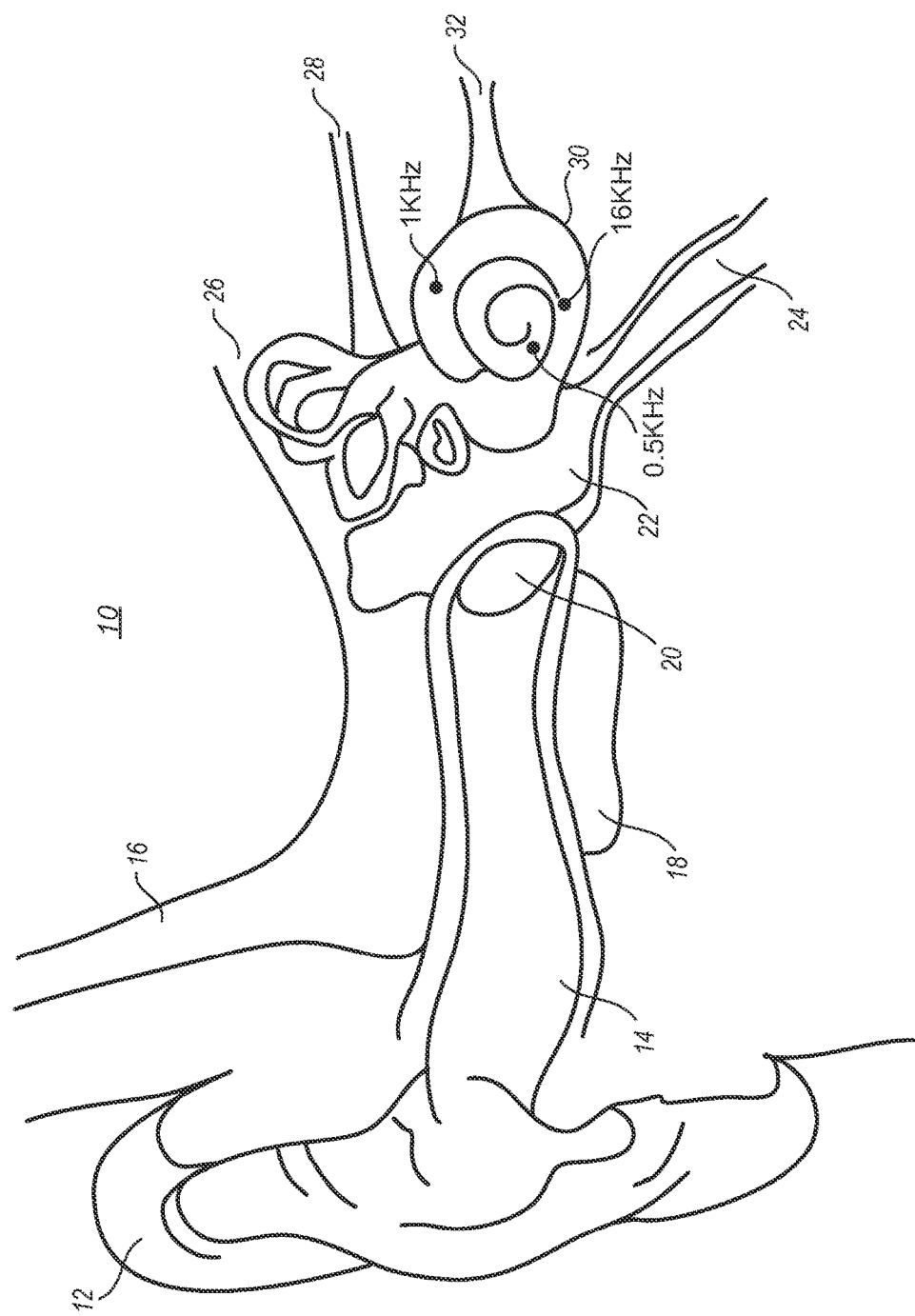
FIG. 1 illustrates the anatomy of the human ear.
Figure 2A:
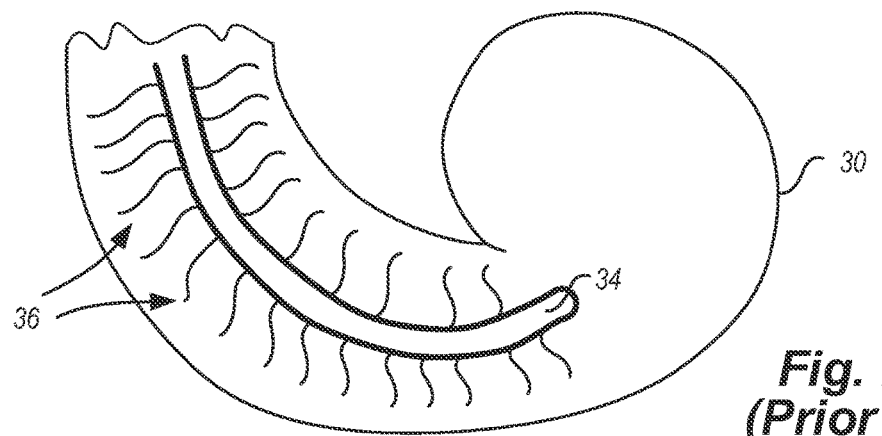
FIGS. 2A-2C illustrates different portions of the cochlea.
Figure 2B:
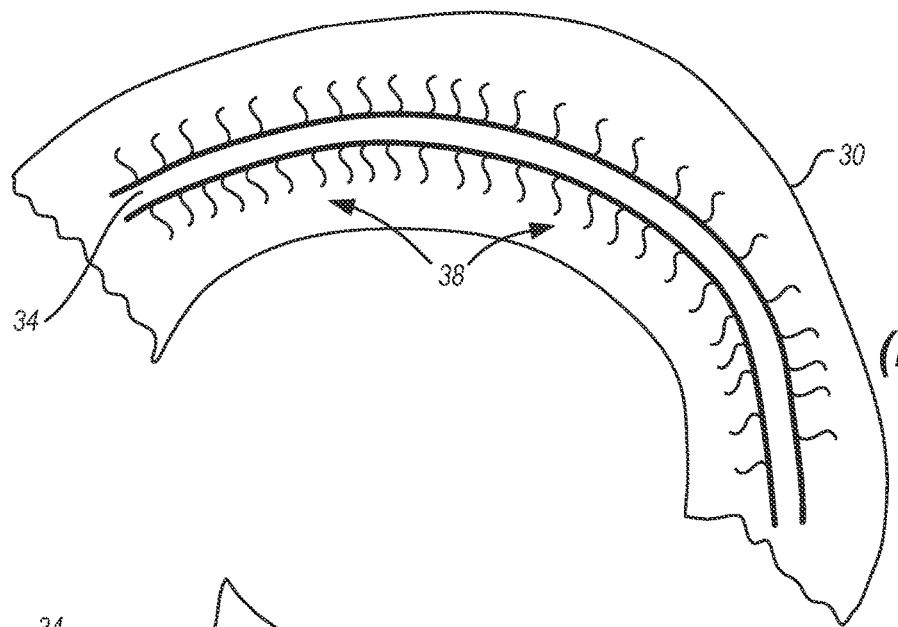
Figure 2C:
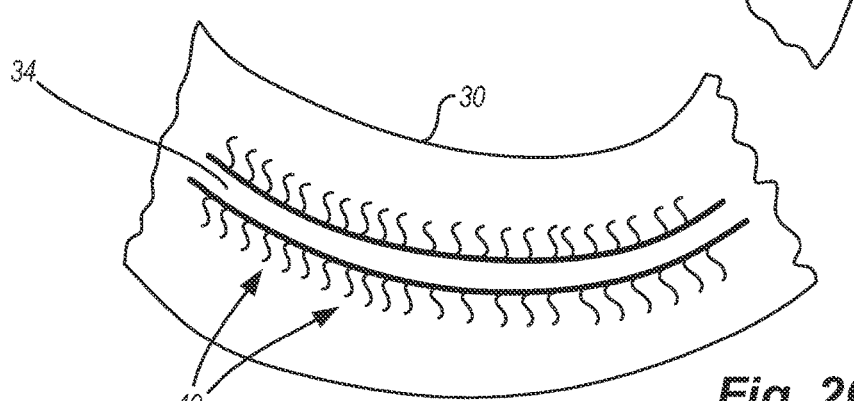
Figure 3:
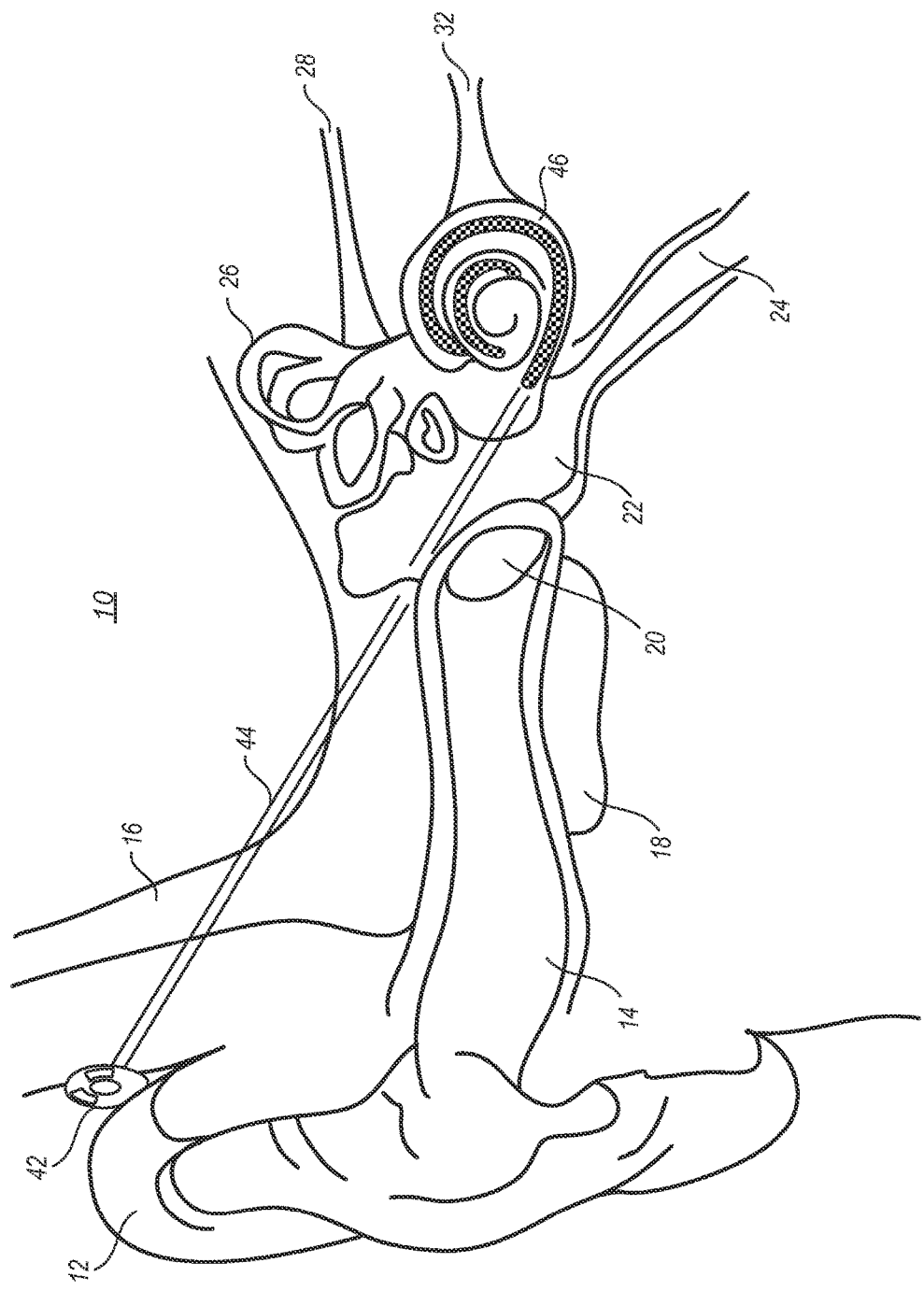
FIG. 3 illustrates a cochlear electrode array implanted in a human cochlea.
Figure 4A:
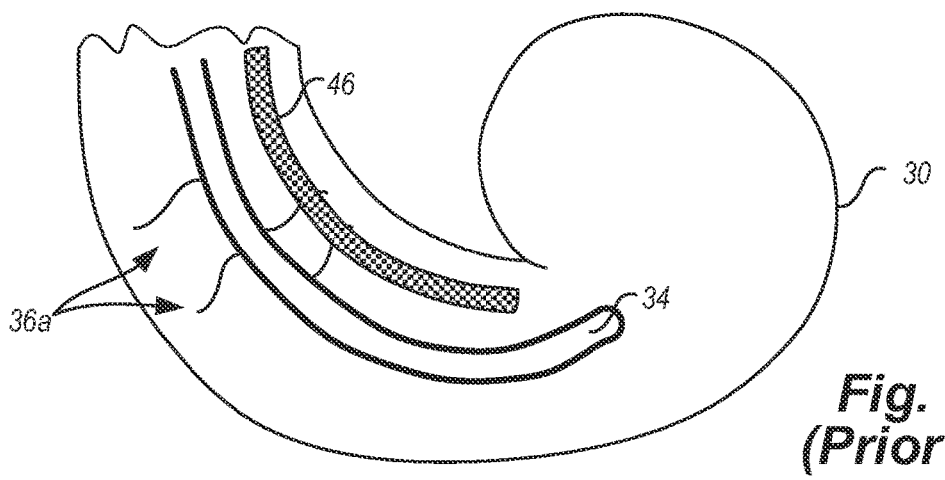
FIGS. 4A-4C illustrates different portions of the cochlea with damage.
Figure 4B:
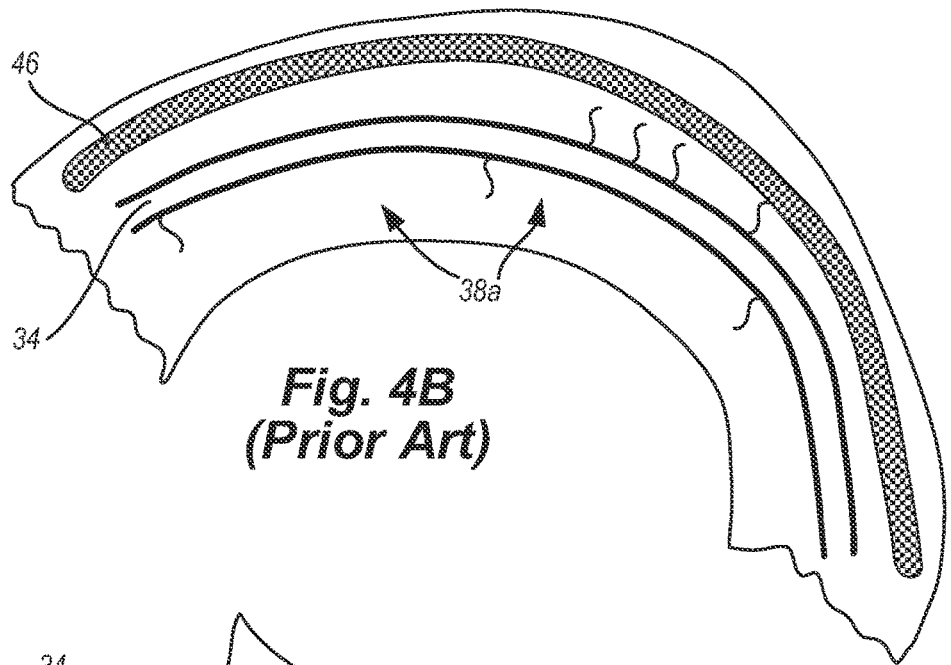
Figure 4C:
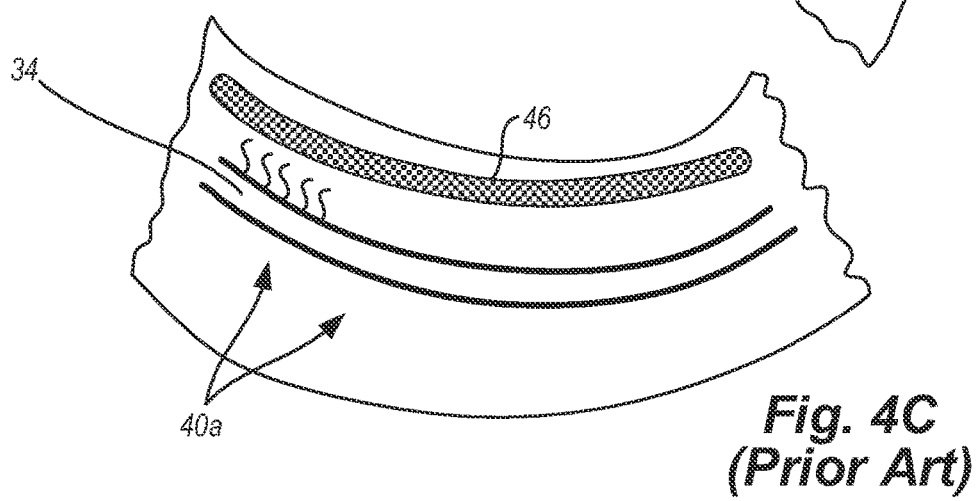

FIGS. 4A-4C illustrates different portions of a damaged cochlea 30. The cochlea 30 in FIGS. 4A-4C may have been affected by the implantation of a cochlear electrode array 46. Alternatively, or in addition, the cochlea 30 may have been affected by some other type of damaging trauma (e.g., blast-induced trauma, noise-induced trauma, pressure waves, extreme fever, infection, and the like). In the illustrations, portions of the cilia 36, 38, 40, and cochlear duct 34 have been damaged as the cochlear electrode array 46 was put into place. Injury to other parts and structures in the middle and inner ear (e.g., the cochlea 30 and other vestibular organs) may have also occurred. In some cases, damage to the middle and inner ear occurs when the cochlear electrode array 46 is passed during a medical procedure. In other cases, the insertion of the cochlear electrode array 46 injures parts of the cochlea 30, but the damage occurs as a result of not treating the injury.

For example, it is believed that passing a cochlear electrode array 46 through the cochlea injures parts of the cochlear duct 34. The injury causes inflammation, abrasion, and other effects to the cochlear duct 34. If the injury is not treated, then the injured portions of the cochlear duct 34 may never recover. In addition, affected cilia may also die off or otherwise lose the ability to vibrate and transfer sound waves into electrical signals detectable by the cochlear nerve 32.

In some cases, a patient has partial hearing loss. For example, the patient may be unable to detect low frequencies but have some ability to hear mid-range and high frequencies. In this case, if a medical procedure to place a cochlear implant damages the base or middle sections of cochlear structures, the patient may gain the ability to hear low frequency sounds, but lose some of their ability to hear mid-range and high frequency sounds. The reduction of mid- and high-frequency hearing sensitivity in this case is a negative effect of the cochlear implant medical procedure. The overall outcome for the patient may be favorable, but the outcome would be better if the negative effect were reduced or eliminated.

Mild hypothermia in the range of about 2° to 6° Celsius has been shown to have neuroprotective qualities when induced during and after an ischemic or traumatic central nervous system injury. A decrease in core temperature of merely one or two degree decrease Celsius may be sufficient to observe these neuroprotective qualities.

One micro-Peltier device created for local cooling purposes to treat traumatic brain injuries is described in U.S. Patent Number 2003/0028229A1 to Rothman. The Rothman device requires a heat sink proximal to the hot junction of the micro-Peltier device. The heat sink renders the Rothman device impractical for small cavity applications because the heat sink size is much larger than the Peltier itself.

Other technology and prior art exists for systemic cooling, such as water beds, which can lower a patient's core temperature. However, by lowering core temperature, adverse side effects may be observed. For example, a slow rate of return to normothermia may cause anti-therapeutic effects, thereby reducing the benefit of hypothermia.

Several other systems to reduce temperature are also known. These other known systems provide advantages and challenges, and only some systems may be beneficial for therapeutic use. For example, refrigerators and air conditioners provide cooling, but the compressors, condensers, and large quantities of liquid refrigerant are generally undesirable in a medical environment.

One device that overcomes the challenges of typical refrigerators and air conditioners is a thermoelectric cooling (TEC) system; sometimes referred to as a Peltier device. The TEC system provides cooling through solid-state electronics, DC power, heat sinks, and semiconductors. A TEC device has no moving parts and therefore operates quietly and reliably for a long time. The TEC system is also small and lightweight, and the TEC system provides electronic control of a temperature gradient within a desirably narrow range.

Figure 5:
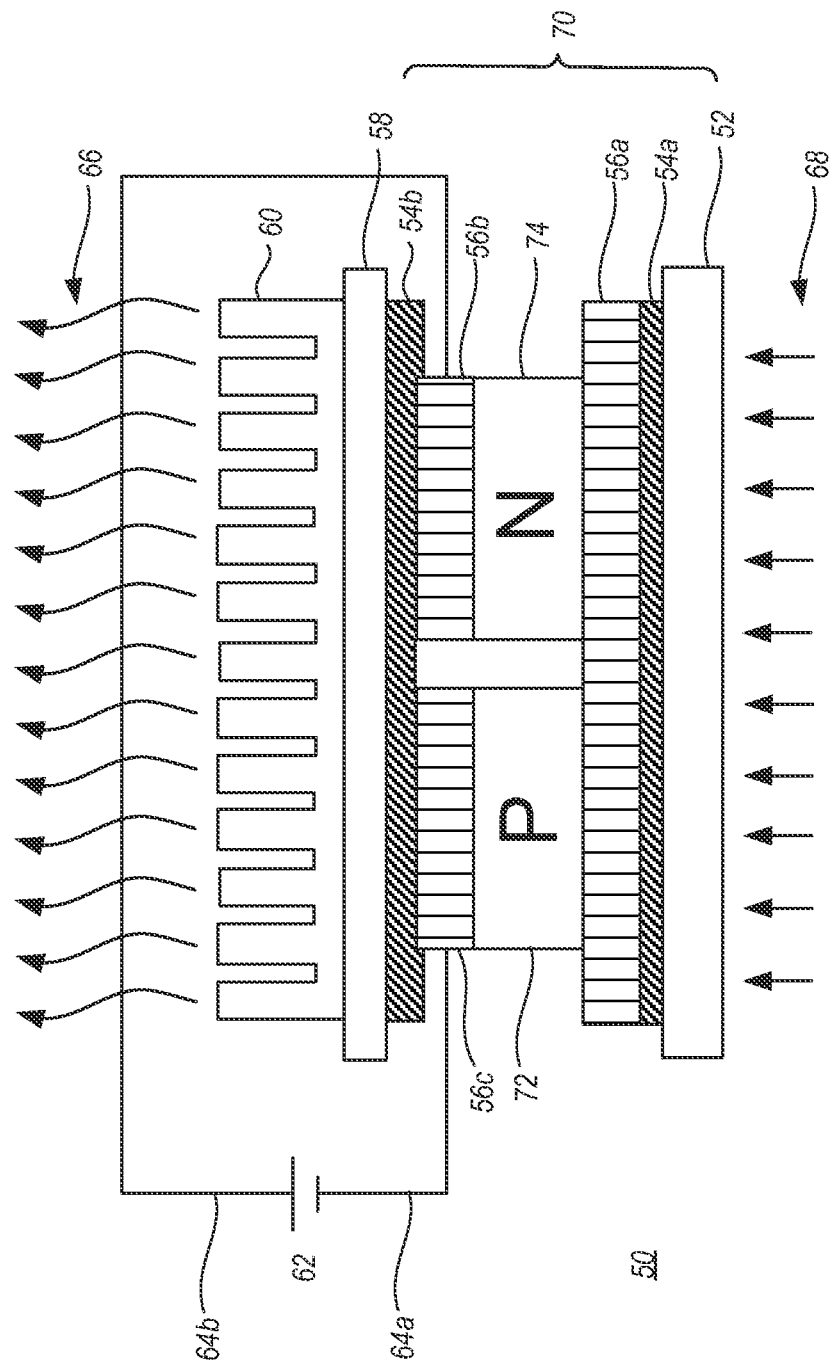
FIG. 5 is a thermoelectric cooling device schematic diagram.

FIG. 5 is a thermoelectric cooling device 50 schematic diagram. A cooling surface 52 is separated from a first conductor layer, the PN conductor 56a, by a first electrical insulator layer 54a. A second surface, the opposite surface 58, is separated from a second conductor, the N conductor 56b, and third conductor, the P conductor 56c, by a second electrical insulator layer 54b. A semiconductor "P" material 72 is formed between the PN conductor 56a and the P conductor 56c. A semiconductor "N" material 74 is formed between the PN conductor 56a and the N conductor 56b.

In FIG. 5, the cooling surface 52 and the opposite surface 58 each have an adjacent electrical insulation layer 54a, 54b, respectively. Between the two electrical insulation layers 54a, 54b, a potential electric current path is formed by a P conductor 56c, a semiconductor "P" material 72, a PN conductor 56a, a semiconductor "N" material 74, and an N conductor 56b. The potential current path in FIG. 5 is sourced by a direct current (DC) power supply 62 and completed with a negative supply conductor 64a coupled to the P conductor 56c and a positive supply conductor 64b coupled to the N conductor 56b.

When current is applied to the TEC device 50 of FIG. 5, bias-inducing electrons flow from the semiconductor P material 72, through the PN conductor 56a, and into the semiconductor N material 74. Biasing the PN junction in this way creates a temperature gradient between the cooling surface 52 and the opposite surface 58. If the positive and negative terminals of the power supply 62 were reversed, then the opposite current flow would generate a temperature gradient in the opposite direction.

In the configuration of FIG. 5, when current is applied, the cooling surface 52 will realize a lower temperature than that of the opposite surface 58. The speed at which the temperature gradient between the cooling surface 52 and the opposite surface 58 reaches an upper limit is based on the amount of current passing through the semiconductors. Accordingly, one mechanism of control of the temperature gradient is a control of the power supply 62.

A second mechanism that affects the temperature gradient between the cooling surface 52 and the opposite surface 58 is the temperature proximate the two surfaces. If the cooling surface 52 is surrounded by a cool temperature, then equilibrium in the circuit will be reached more quickly. Along these lines, if the opposite surface 58 is surrounded by a warm temperature, then equilibrium is reached more quickly. Accordingly, if the TEC device 50 is desirably providing a cooling function, then removal of the heat from the opposite surface 58 will provide more aggressive cooling at the cooling surface 52.

As illustrated in FIG. 5, heat is absorbed 68 at the cooling surface 52. Heat is released 66 at a heat sink 60 coupled to the opposite surface 58. The addition of heat sink 60 to the opposite surface 58 permits a more aggressive heat release than otherwise available.

A third mechanism that affects the temperature gradient between the cooling surface 52 and the opposite surface 58 is the number of the P and N semiconductor pairs. A higher number of junctions across which electrons will flow provide a faster response and larger temperature gradient to be achieved.

Figure 6:
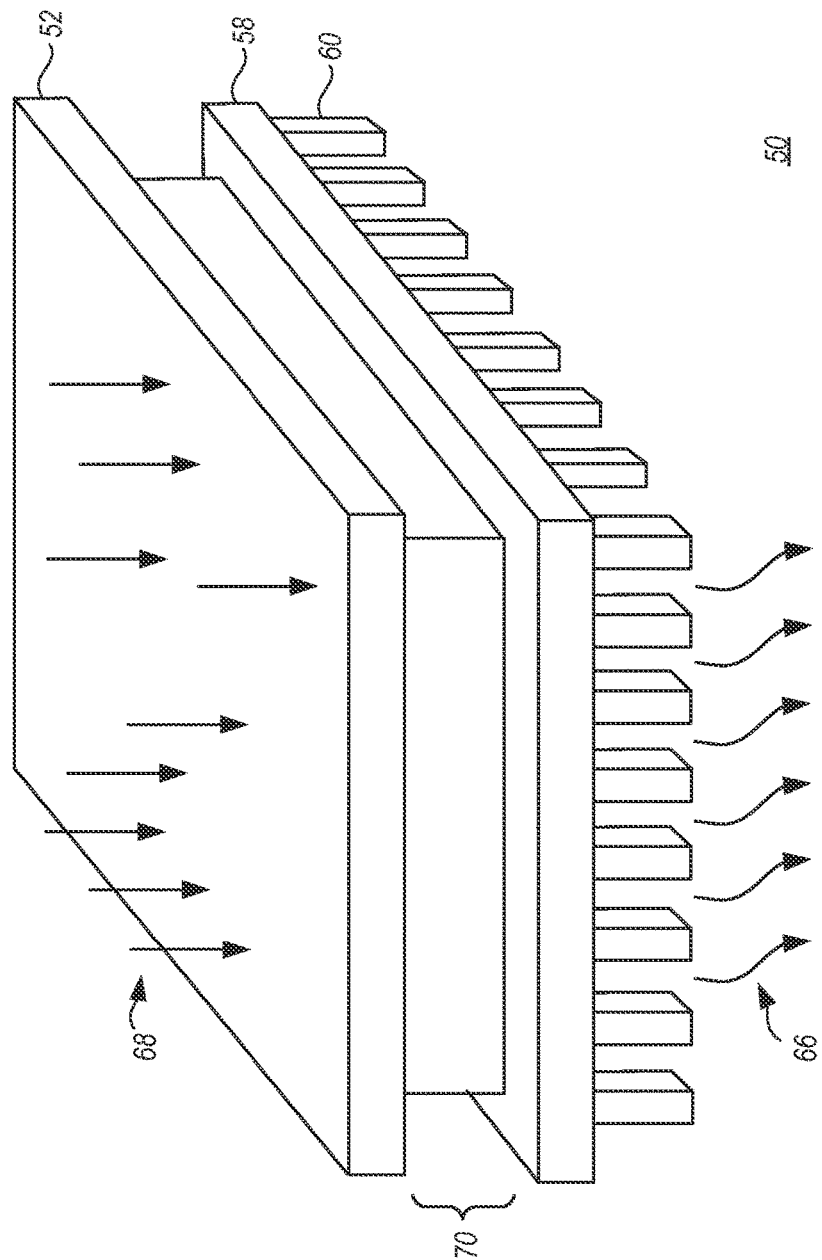
FIG. 6 is a perspective view of the thermoelectric cooling device of FIG. 5.

FIG. 6 is a perspective view of the thermoelectric cooling (TEC) device 50 of FIG. 5. The TEC device 50 of FIG. 6 is "upside-down" relative to the device in FIG. 5. From the topside perspective, heat is absorbed 68 into the cooling surface 52 as inspired by current flowing through the Peltier stack 70 (formed of electrical insulators 54a, 54b, conductors 56a, 56b, 56c, and PN materials 72, 74). The heat transferred to the opposite surface 58 is released 66 through the heat sink 60.

Turning back to trauma incident on living tissue, for example as caused by medical procedures, it has been shown that generally administered mild hypothermia provides therapeutic benefits. It is now recognized and described herein that after diligent experimentation and testing, localized hypothermia can be shown to provide benefits with a reduced effect on other biological phenomena and immune response.

With respect to middle and inner ear trauma, a non-limiting therapeutic device and method has been developed to provide localized hypothermia proximate to a site of damage or potential damage. In an exemplary cochlear implant procedure, beneficial effects were provided to specific neural pathways of interest, and little or no negative effects on other biological phenomena or immune response was observed. In the exemplary procedure, the therapeutic device was used to reduce biological temperature in a small surgical cavity about 6 mm$^3$.

Figure 7:
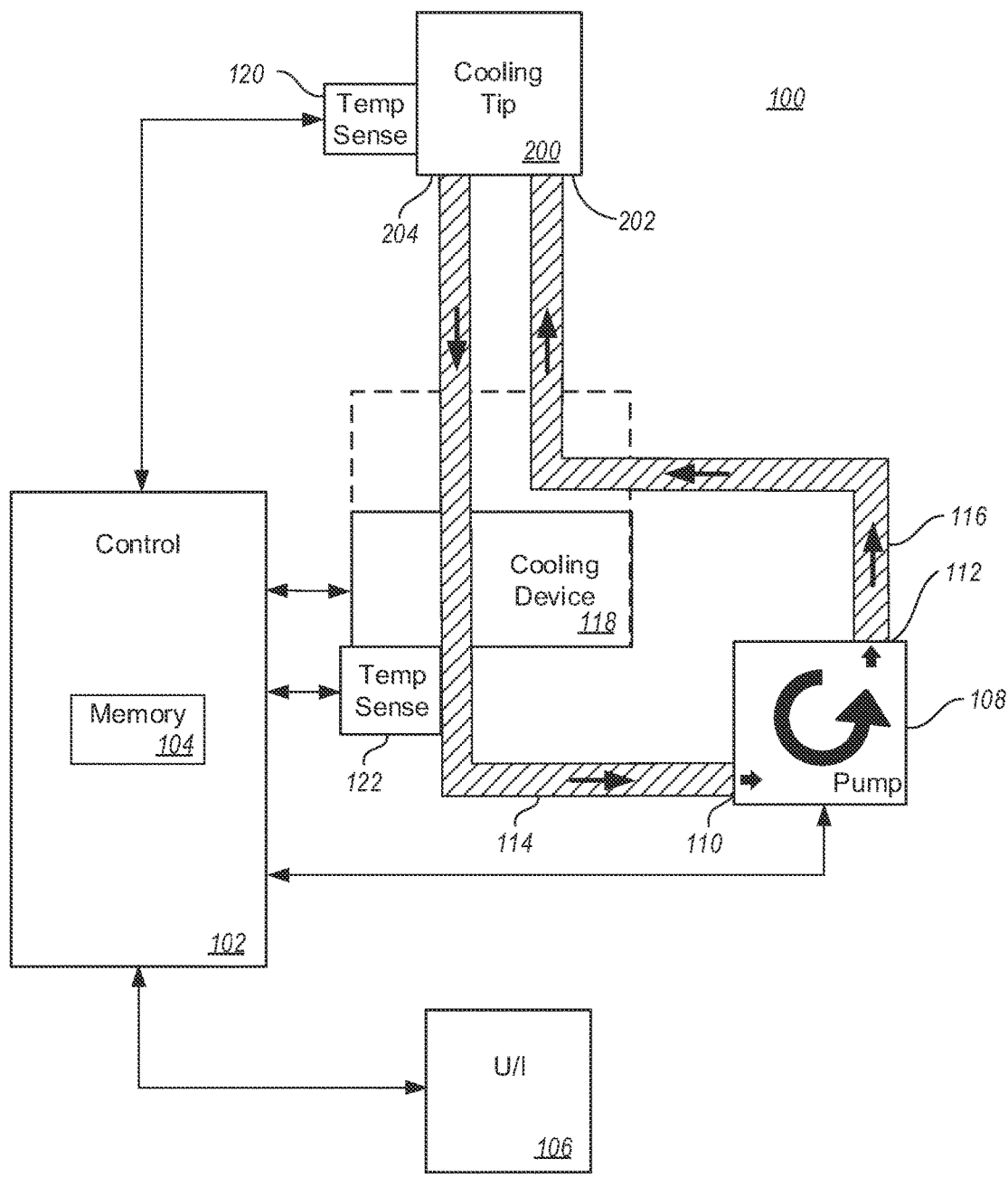
FIG. 7 illustrates a localized therapeutic hypothermia system block diagram.

FIG. 7 illustrates a localized therapeutic hypothermia system 100 block diagram. The system of FIG. 7 was employed in the exemplary cochlear implant procedure. The system of FIG. 7 is non-limiting and may be used in other medical procedures.

A control system 102 directs operations of the localized therapeutic hypothermia system 100. The control system 102 includes a processor such as a microcontroller. The control system 102 is illustrated in FIG. 7 having a memory 104. The memory 104 may be wholly or partially embedded in the control system 102, or alternatively, the memory 104 may be partially or completely external to the control system 102. The memory is configured to store parameters and software instructions executable by the processor of the control system 102.

An optional user interface (U/I) 106 is configured to provide a mechanism for external control and reporting of the localized therapeutic hypothermia system 100. For example, the U/I 106 may include a lamp or light emitting diode (LED) that is illuminated when the localized therapeutic hypothermia system 100 is operating or sensing a determined condition. Different light sources or a light source of multiple colors may provide different status indications of the localized therapeutic hypothermia system 100. For example, one color may indicate that the system is operating while another color may indicate that the system has achieved a desired temperature, temperature gradient, or temperature differential. As an alternative or in addition to light source indicators, the U/I 106 may include a display that provides additional status reporting such as input temperature setting, output temperature achieved, power consumption, elapsed time or some other time measure, and the like.

The U/I 106 may further include input mechanisms to control the localized therapeutic hypothermia system 100. For example, a desired temperature setting may be input, a measure of time may be input, an approximate size of the cavity where the device will be operating may be input, and many other parameters may also be input. In these cases, the control system may store the input values in the memory 104 and access the values during program execution. In one example, a user enters a desired target temperature to achieve. The user may optionally enter threshold values such that a hysteresis function will more efficiently control the achieved temperature within a window of operation.

A pump 108 includes a pump input port 110 and a pump output port 112. In some cases, the pump 108 is a positive displacement pump such as a peristaltic pump. In other cases, the pump 108 is a direct lift pump or a gravity pump. In the exemplary embodiment of FIG. 7, the pump 108 is configured to move a fluid in a closed system such that the fluid does not contact any of the electric or mechanical structures of the pump. In FIG. 7, the pump 108 receives a fluid into the input port 110 and passes the fluid out of the output port 112. A control line indicates that operations of the pump 108 may be directed by the control system 102, and in some cases, pump 108 provides operational information back to the control system 102.

The fluid that is fed into pump 108 and out from the pump 108 passes through first and second fluid lines 114, 116, respectively. The first and second fluid lines 114, 116 may be removably coupled to the input port 110 and output port 112 respectively.

In the exemplary embodiment, the fluid that passes through pump 108 is a fluorocarbon. In other cases, the fluid is a different biocompatible liquid having a high thermal resistivity. The fluid is used in the localized therapeutic hypothermia system 100 as a coolant. In some cases, the fluid that passes through pump 108 is the primary coolant in the system. In these cases, one or more other fluids may also be used in other parts of the system as secondary coolants.

The fluid that is pumped through the localized therapeutic hypothermia system 100 of FIG. 7 passes through a cooling tip 200. Fluid is passed into the cooling tip 200 through a cooling tip input port 202. The second fluid line 116 is fixedly or removably coupled to the cooling tip input port 202. Fluid is passed out from the cooling tip 200 through a cooling tip output port 204, to which the first fluid line 114 is fixedly or removably coupled.

Generally speaking, the cooling tip 200 includes a small cavity formed within a structure having thermally conductive properties. In some embodiments, the cooling tip consists solely of the structure having the small cavity. In other embodiments, the cooling tip 200 may include one or more catheters, one or more flexible or rigid tubes (e.g., "probes"), valves, priming ports, fluid filling ports, fluid emptying ports, temperature sensors, fluid flow volume sensors, pressure regulators, volumetric control devices, micro-electromechanical (MEMS) devices such as accelerometers, and other like structures.

When the fluid flows through the cooling tip 200, heat from the area proximate to the cooling tip is passed through the thermally conductive structure and absorbed by the fluid. As the fluid circulates out of the cooling tip 200, the absorbed heat is also carried out of the cooling tip 200.

Fluid that is circulated out of the cooling tip 200 passes through or alongside a cooling device 118 before returning to the pump 108. The cooling device 118 is configured to dissipate or otherwise remove the heat energy absorbed by the fluid. In some cases, the cooling device 118 is a thermoelectric cooling (TEC) device. In some cases, the cooling device 118 is a water bed system. In some cases, the cooling device 118 is a refrigeration system. In yet other cases, the cooling device 118 is some other type of system configured to encourage the fluid to release its absorbed heat.

The cooling device 118 is assembled to affect the fluid passing through the first fluid line 114. Optionally, as illustrated in FIG. 7, the cooling device 118 may also be assembled to affect the fluid passing through the second fluid line 116. When configured to affect the fluid in the second line, the cooling device may allow the fluid to absorb more heat energy thereby providing an increased cooling ability of the localized therapeutic hypothermia system 100.

The localized therapeutic hypothermia system 100 embodiment of FIG. 7 includes two or more optional temperature sensing devices. A first optional temperature sense device 120 is assembled near or within the cooling tip 200. The first temperature sense device 120 is arranged to provide a temperature signal to the control system 102. The temperature signal is generally linearly proportional to the temperature at and proximate to the cooling tip 200. In some cases, the first temperature sense device 120 is configurable (e.g., for calibration, testing, for setting a factory default profile, and the like). In such cases, the control system 102 may bi-directionally communicate data to and from the first temperature sense device 120.

A second temperature sense device 122 may optionally be provided near or within the cooling device 118. Along the lines of the first temperature sense device 120, the second temperature sense device 122 is arranged to provide to the control system 102 a temperature signal that is linearly proportional in the vicinity of the cooling device 118. The second temperature sense device 122 may provide temperature signals associated with the cooling device 118, the fluid within the first or second fluid line 114, 116, the ambient air, or some other temperature signal.

The localized therapeutic hypothermia system 100 illustrated in FIG. 7 may be further described by way of a second exemplary embodiment. The second embodiment is described with additional details, though it is understood the second embodiment is non-limiting and different variations are contemplated without departing from the inventive concepts described throughout the disclosure.

In the second exemplary embodiment, the cooling tip 200 and fluid lines 114, 116 are fixedly assembled into a sterilizable medical device. The sterilizable medical device is arranged to lower the biological temperature in a small cavity (e.g., a surgical cavity) where beneficial cellular responses and functionally-protective therapeutic results can be achieved with applied localized hypothermia.

In the second embodiment, the control system 102 is a Peltier Temperature Controller System (PTCS), the pump 108 is a Peristaltic Pump System (PPS), and the cooling device 118 is a TEC. The components in the embodiment are particularly arranged with distinct characteristics to achieve the desired temperature range of the traumatized or potentially traumatized site.

The fluid in the second embodiment is a fluorocarbon, though other fluids may also be used, and the system formed by the cooling tip 200 and the first and second fluid lines 114, 116 is a closed, primed system. Since the pump 108 is a peristaltic pump, the first and second fluid lines 114, 116 form a single, continuous fluid line. Due to the priming of the system in a closed circuit, the fluorocarbon is rapidly cooled and recycled, in turn cooling the cooling tip 200.

In order to cool the fluorocarbon, the liquid is passed through the cooling junction of the TEC (i.e., cooling device 118 in this second embodiment). The TEC in this case is formed as a Heating/Cooling Perfusion Cube (HCPC), which includes a reservoir for the liquid. The cooling junction of the TEC becomes cold when an input current of known value as directed by the PCTS (i.e., control system 102 in this embodiment) creates a temperature potential between the cold junction (material type 1) and its counterpart, the hot junction (material type 2).

In the present exemplary second embodiment, the fluorocarbon primary coolant passes through the HCPC, which includes both hot and cold junctions. In order for the fluorocarbon coolant to be unaffected by the hot junction, a secondary coolant is circulated in proximity to the hot junction of the HCPC. The secondary coolant may also be fluorocarbon, or the second coolant may be some other cooling medium.

In the second embodiment, a user directs a desired temperature of the cold junction of the HCPC via an input provided though the U/I 10. A thermistor in the HCPC acts as an effector to encourage the desired temperature. The thermistor may be embodied as the second temperature sense device 122. Once the fluorocarbon in the HCPC reservoir is cooled to its target temperature, sensed by the thermistor in the HCPC, the fluorocarbon travels through the peristaltic pump 108 to the cooling tip 200 of the medical device.

The medical device is comprised of an insulated, multi-lumen catheter and a copper tip (i.e., cooling tip 200) acting as a small reservoir for the fluorocarbon. The fluorocarbon travels down a first lumen (i.e., second fluid line 116) of the insulated catheter, enters the copper tip, and travels back through the second lumen (i.e., first fluid line 114) of the catheter.

A second thermistor is embodied as the first temperature sense device 120. The second thermistor, which is integrated with or assembled proximal to the copper tip, is responsive to the therapeutic temperature of the surgical site. The therapeutic temperature is the desired temperature to induce localized mild hypothermia. This therapeutic temperature at the copper tip is often different from the temperature sensed at the HCPC because heat energy is gained when the fluorocarbon travels through the catheter.

After passing through the copper tip (i.e., cooling tip 200), the fluorocarbon coolant is recycled. The recycling, or flow of the fluid, results from the pressure exerted by the PPS. In this second embodiment, the PPS is comprised of a motor with three cylindrical bearings pushing the fluorocarbon along the catheter (i.e., first and second fluid lines 114, 116) and back to the HCPC. A potentiometer allows for variable speed of the PPS motor, which correlates to specific volume flux of fluorocarbon coolant through the closed, primed circuit. In the second embodiment, the potentiometer may provide either direct input to the PPS, or the potentiometer may provide input to the control system 102, which then directs the operation of the PPS.

An alternative of the second embodiment includes a micro-Peltier and a micro-controller to drive the micro-Peltier. In this case, electrically insulated drive circuitry connects the micro-controller and the micro-Peltier device, which will be coupled to a metal portion of the cooling tip 200. In such a configuration, the cooling tip 200 would act as a heat sink for the hot junction of the Micro-Peltier.

Another alternative of the second embodiment includes a customization of the micro-Peltier surface formed with the cooling tip 200. The cooling tip 200 surface can be customized to mate with a particular bone, organ, muscle, or other biological matter depending upon its application. Customization of the cooling tip 200 micro-Peltier surface can be based on the surface area and shape of the loci to be cooled and the desired temperature differential.

Figure 8:
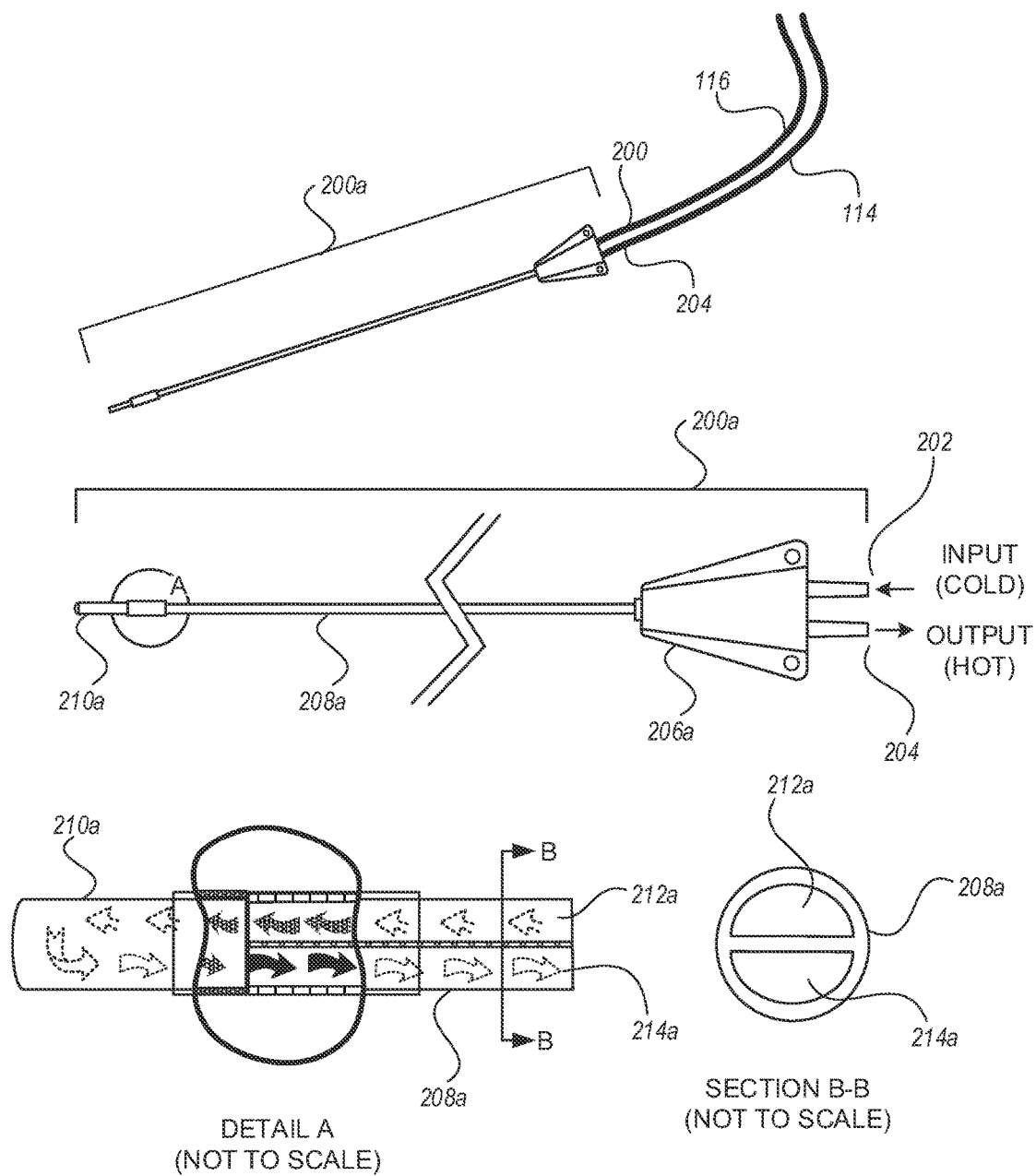
FIG. 8 is a medical device assembly configured as a first cooling probe embodiment.

FIG. 8 is a medical device assembly configured as a first cooling probe embodiment 200a. First and second fluid lines 114, 116 respectively are attached to a first tubing manifold/catheter interface 206a of the first cooling probe embodiment 200a. The first fluid line 114 is attached at a cooling tip output port 204, and the second fluid line 114 is attached at a cooling tip input port 202.

The first tubing manifold/catheter interface 206a is arranged to receive a first multi-lumen catheter 208a. In some cases the first multi-lumen catheter 208a is formed of a soft, flexible rubber-type or plastic-type material. In other cases, the first multi-lumen catheter 208a is formed of another material. The material used to form the first multi-lumen catheter 208a is biocompatible with a typical human body. In one exemplary embodiment, the multi-lumen catheter 208a is formed from polytetrafluoroethylene/polyetherether ketone (PTFE/PEEK) tubing, 0.98 mm inside diameter (ID), 2.03 mm mean diameter (MD), and 2.20 mm outside diameter (OD) having an MD/OD length of about 50 cm, and an ID length of 100+cm. The tubing of the first multi-lumen catheter 208a may be threaded with, for example, 1.00 mm threads arranged to receive a metal (e.g., copper) threaded cap, the surface of which may also be treated with a biocompatible material.

In some cases, the first multi-lumen catheter 208a includes or is formed with a material that has thermal insulating properties. In such embodiments, the outer surface of the first multi-lumen catheter 208a will typically remain smooth enough to easily slide over living biological matter without substantial friction or abrasion. That is, the outer surface of the first multi-lumen catheter 208a is formed to avoid discomfort to the patient. Along these lines, some embodiments of the first multi-lumen catheter 208a are formed or assembled within an enveloping smooth, low friction, biocompatible sheath.

The first multi-lumen catheter 208a may be highly malleable such that its shape is dictated by gravity and any adjacent supportive structures. Alternatively, the first multi-lumen catheter 208a may be workably malleable such that the device can be desirably bent into position and desirably rigid so as to overcome gravity and support its own weight without additional support structures when bent into position. In yet other cases, the first multi-lumen catheter 208a is substantially rigid and a force sufficient to overcome the rigidity will damage or destroy the device.

The first multi-lumen catheter 208a is coupled to a first cooling chamber 210a. The first cooling chamber 210a is formed from a thermally conductive material. In some cases, the first cooling chamber 210a is formed from copper, aluminum, platinum, palladium, gold, or a metallic alloy. In other cases, the first cooling chamber 210a is formed from a thermally conductive composite or plastic material such as one impregnated with a conductive metal or other material. The material of the first cooling chamber 210a may, for example, be industrially available as a thermally conductive plastic or polymer.

The surface of the first multi-lumen catheter and the surface of the cooling chamber 210a may be treated or otherwise formed with a bio-compatibility agent such as silicone, polytetrafluoroethylene (PFTE, or TEFLON), or parylene. Other materials may also be used. In addition to preventing negative reactions with human biology, the biocompatibility agent may also provide increased lubricity, a platform to distribute a therapeutic agent such as a bacterial growth inhibitor, surface protection for coated structures, and other benefits.

The embodiment of FIG. 8 includes particular details of the first multi-lumen catheter 208a and the first cooling chamber 210a. Detail "A" illustrates a cut-away view of the area where the first multi-lumen catheter 208a joins the first cooling chamber 210a. Detail "B-B" illustrates a cross-section view of the first multi-lumen catheter 208a.

Illustratively, in Detail A, a fluid having a lower temperature flows from right to left through a first (top) lumen 212a of the first multi-lumen catheter 208a. The fluid enters the first cooling chamber 210a, circulates, absorbs heat energy, and exits the first cooling chamber 210a. Upon exiting, the fluid, which now has a higher temperature, passes through a lower (bottom) lumen 214a of the first multi-lumen catheter 208a. For ease in understanding the drawing, the bio-compatibility agent is not shown. The fluid in FIG. 8 is a fluorocarbon, but some other heat absorptive fluid could also be used.

When the medical device of FIG. 8 is used in a medical procedure, the cooling tip 200a is placed in the vicinity of a surgical locus. The first cooling chamber 210a is typically placed in contact with the area of tissue, bone, muscle, or other biological material where cooling is desired. The fluid circulates through the cooling tip 200a and absorbs heat from the proximal area, thereby cooling the area of the surgical locus.

The particular procedure being performed will often guide the parameters of use of the medical device. The types of parameters controlled may include a length of time prior to the medical procedure that the cooling chamber 210a is applied, the rate of flow of the fluid, the physical distance between the cooling chamber 210a and the point of surgical trauma, and other factors.

Figure 9:
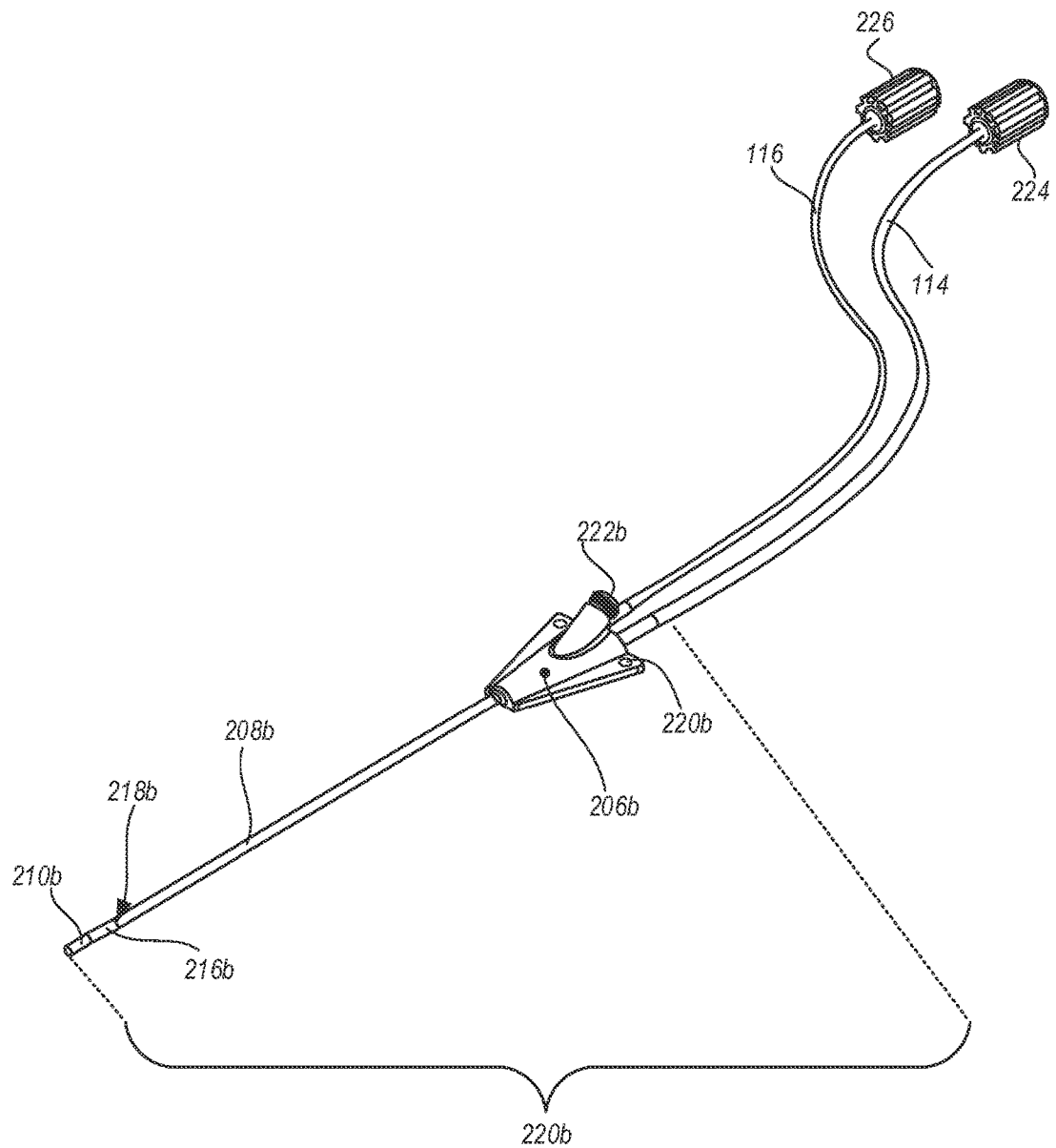
FIG. 9 is another medical device assembly configured as a second cooling probe embodiment.

FIG. 9 is another medical device assembly configured as a second cooling probe embodiment 200b. The medical device of FIG. 9 provides localized temperature regulation of tissue in an area within a human body. The first and second fluid lines 114, 116 are coupled to the second cooling probe embodiment 200b and other components of a localized therapeutic hypothermia system.

The coupling of the fluid lines to the cooling probe is by way of a tubing manifold/catheter interface 206b. The embodiment of FIG. 9 includes manifold mounting holes 220b, which may be used to fixedly or removably secure the assembly to a structurally sound base. The tubing manifold/catheter interface 206b further includes a manifold vent port 222b. The manifold vent port 222b can be configured with a one way valve or another type of valve to "bleed" or prime the fluid flow closed system, thereby removing air or other thermally inefficient materials.

The second cooling probe embodiment 200b is configured with a thermal control catheter (i.e., a second multi-lumen catheter 208b) that is biocompatible and designed to fit within a particular space in the human body. The thermal control catheter has a multi-lumen tubing body formed of plastic, rubber, or some compatible alternative.

The multi-lumen tubing body is terminated at its distal end with a thermally conductive cap (i.e., a second cooling chamber 210b) and at its proximal end with first and second fluid lines 114, 116. The thermally conductive cap is hermetically bonded to the multi-lumen tubing body by an assembly joint 216b and an adhesive sealant 218b. The thermally conductive cap in FIG. 9 is metal, but some other thermally conductive material could also be used. In some embodiments, the thermally conductive cap is treated with a biocompatibility agent.

The first fluid line 114 communicates with a first lumen of the multi-lumen tubing body, and the second fluid line 116 communicates with a second lumen of the multi-lumen tubing body. The first and second fluid lines 114, 116 are respectively terminated with connectors 224, 226.

The capped distal end establishes a fluid flow pathway between some or all of the individual lumens of the multi-lumen tubing body such that a working fluid driven through the catheter can facilitate the transfer of heat, either to or from the body tissue. Flow control and fluid temperature regulation are provided by a fluid control system having a pump, a heating and/or cooling apparatus, a temperature sensor, and a computing processor. Fluid temperature and flow rate are controlled such that the tip of the catheter and the tissue it contacts maintain a desired temperature. The fluid control system may be of the type illustrated in FIG. 7.

Figure 10:
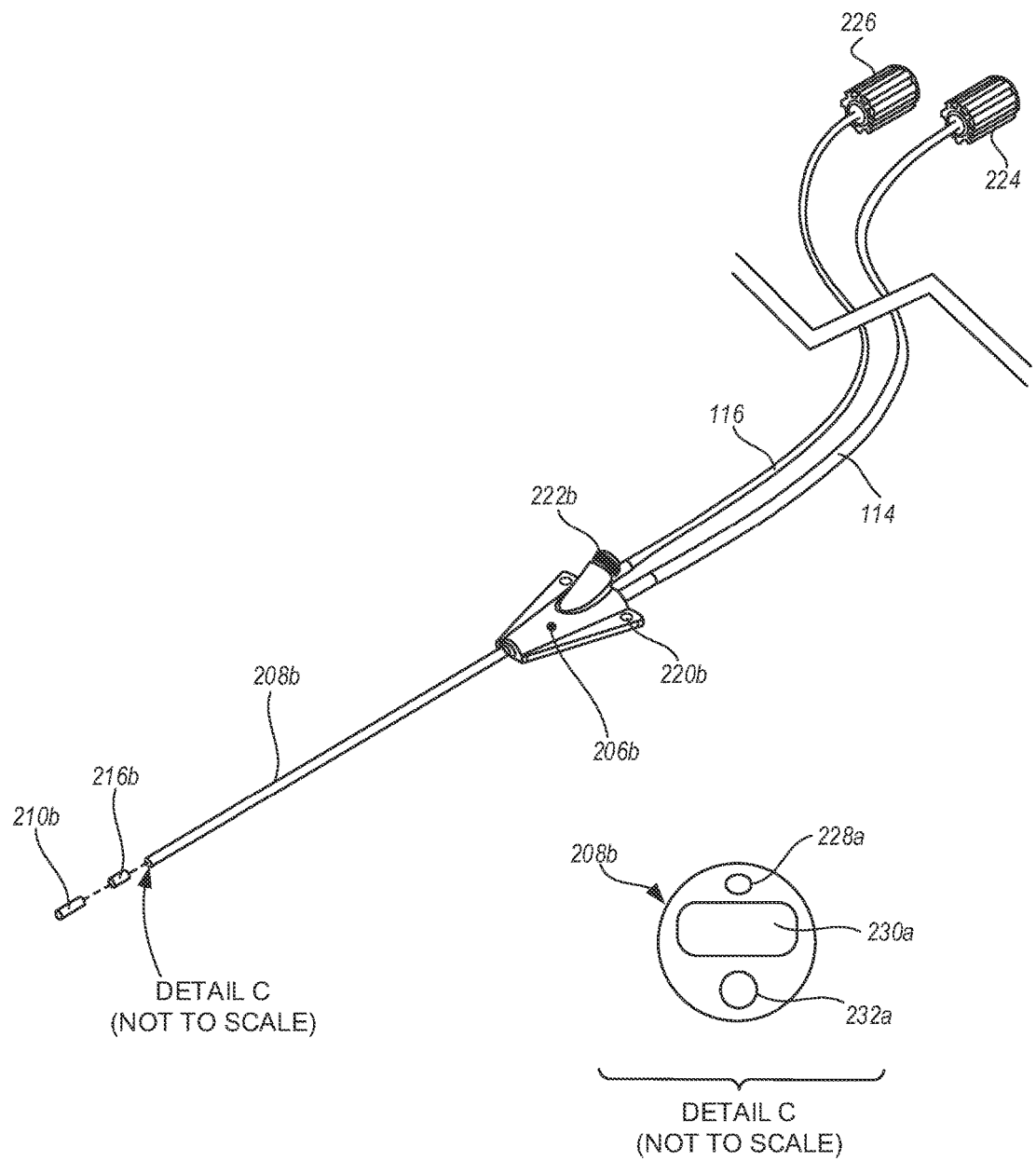
FIG. 10 illustrates the medical device assembly of FIG. 9 with some components shown in greater detail.

FIG. 10 illustrates the medical device assembly of FIG. 9 with some components shown in greater detail. Detail "C" illustrates a cross-sectional view of the area where the second multi-lumen catheter 208b joins the second cooling chamber 210b. As shown in Detail C, the multi-lumen catheter 208b of FIG. 10 includes three lumens, though more or fewer lumens could have been formed. In the multi-lumen catheter 208b, a first lumen 228a is coupled to the manifold vent port 220b. The first lumen 228a is generally un-pressurized and open to the atmosphere when the vent port 220b is open. The second lumen 230a of the multi-lumen catheter 208b and third lumen 232a of the multi-lumen catheter 208b are under pressure when the system is operating. The second and third lumens 230a, 232a form integral parts of the closed fluid flow system.

The cross-sectional areas for each of the three lumens 228a, 230a, 232a may be different from each other and different from the illustration in FIG. 10. Alternatively, two or more of the lumens may have the same shape and volume. The shape and volume of the lumens 228a, 230a, 232a is desirably selected based on the fluid filling characteristics of the thermally conductive cap (i.e., second cooling chamber 210b). For example, to reduce the potential of an air bubble forming or captured in the thermally conductive cap, which will affect the thermal behavior and heat transfer performance of the system, and to further facilitate efficient fluid filling, the size and profile of each lumen relative to other lumens may be different.

Selectively forming the lumens with different shapes, profiles, volumes, or other characteristics may establish specific pressure differential between the different lumens 228a, 230a, 232a. In FIG. 10, the first lumen 228a, which is coupled to the manifold vent port 22b, has a circular cross-section and is very small. The second lumen 230a is non-circular and formed to occupy the largest share of the second multi-lumen catheter 208b. The third lumen 232a is larger than the first lumen 228a, but smaller than the second lumen 230a. In the embodiment, the second lumen 230a is configured to supply a heat-transporting fluid (e.g., fluorocarbon) to the thermally conductive cap, while the third lumen 232a configured to release the fluid from the thermally conductive cap. The arrangement of FIG. 10, which creates a higher pressure in the third lumen 232a, facilitates a complete and persistent filling of the thermally conductive cap with the heat-transporting fluid.

Figure 11:
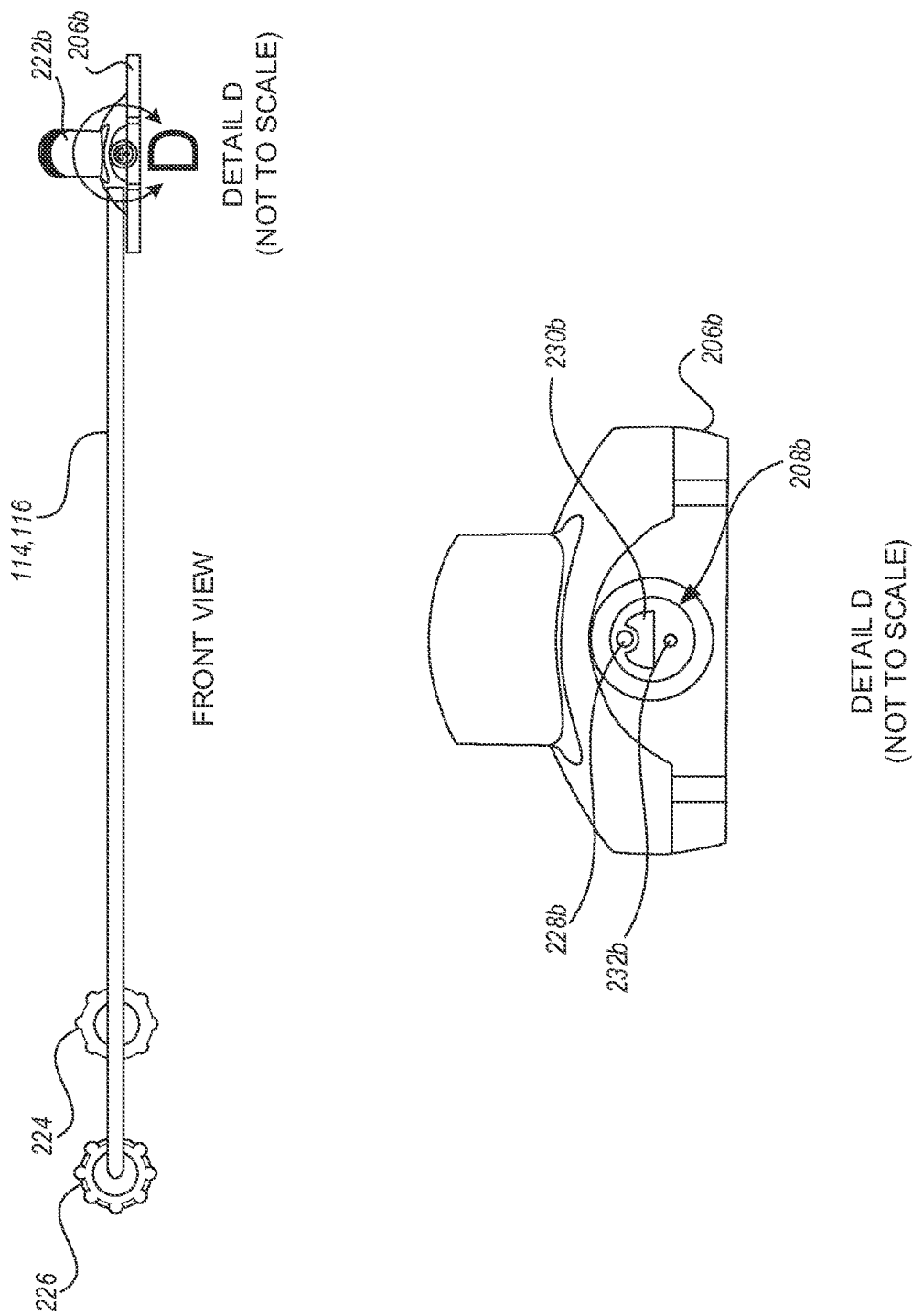
FIG. 11 illustrates a medical device assembly along the lines of FIGS. 9 and 10 with some different components shown in greater detail.

FIG. 11 illustrates a medical device assembly along the lines of FIGS. 9 and 10 with some different components shown in greater detail. Detail "D" illustrates a cross-sectional view of tubing manifold/catheter interface. As shown in Detail D, the multi-lumen catheter 208b of FIG. 11 also includes three lumens. In the multi-lumen catheter 208b of FIG. 11, a first lumen 228b, an up-pressurized lumen, is coupled to the manifold vent port 220b. The second lumen 230b of the multi-lumen catheter 208b in FIG. 11 is the largest lumen, but the second lumen 230b is formed with an irregular cross-sectional shape. The third lumen 232b in FIG. 11 is the smallest of the lumens. Both the second and third lumens 230b, 232b are under pressure and form integral parts of the closed fluid flow system.

Figure 12:
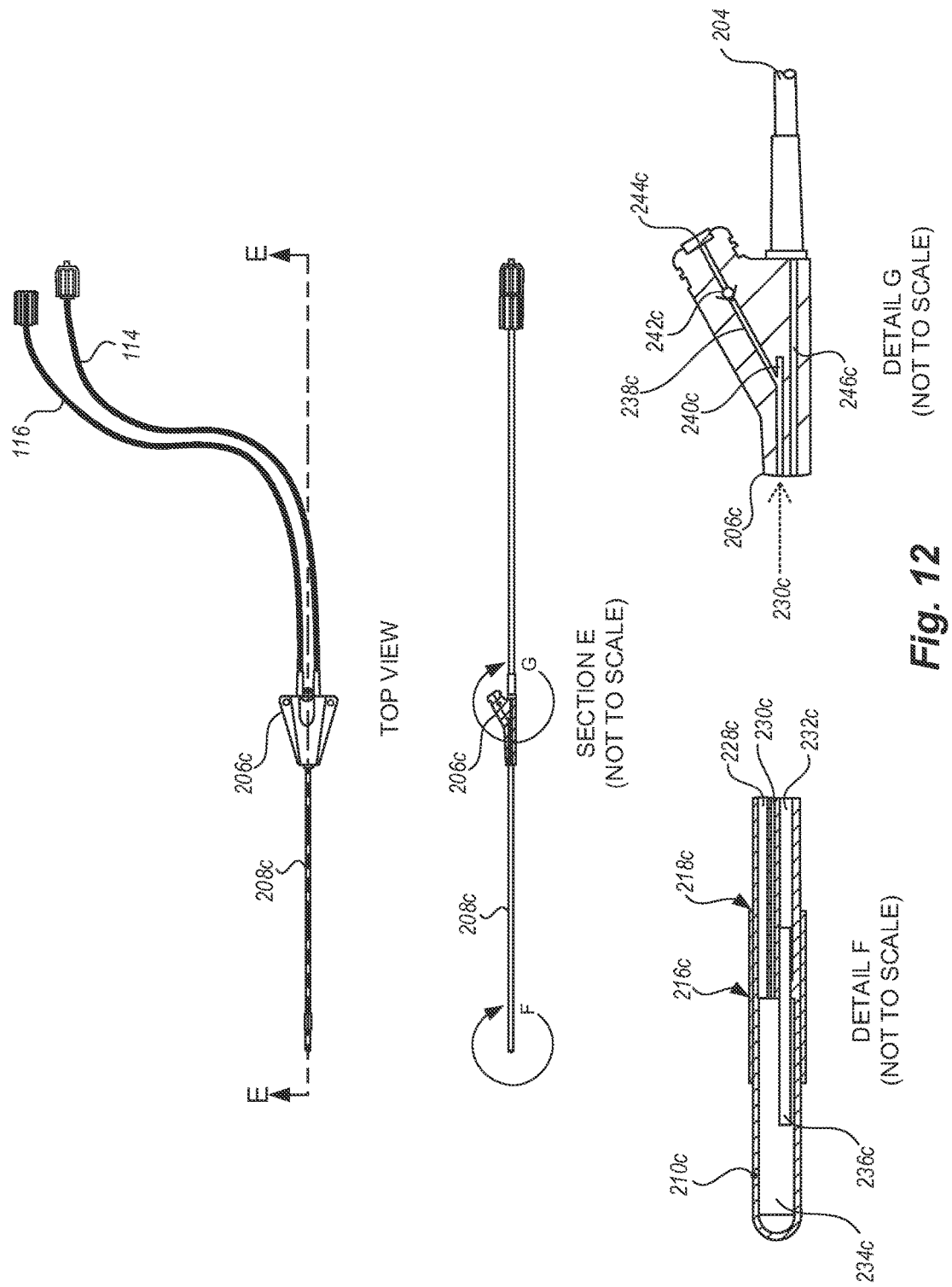
FIG. 12 illustrates another embodiment of a medical device assembly.

FIG. 12 illustrates another embodiment of a medical device assembly. The medical device of FIG. 12 includes a third multiport (i.e., multi-lumen) catheter 208c embodiment and a third tubing manifold/catheter interface 206c. As illustrated in FIG. 12, a cross section E-E is taken from a top view perspective. Two areas of detail are called out; Detail "F" and Detail "G." The cross-section of a third cooling chamber 210c is shown in Detail F. The cross section of a portion of the third tubing manifold/catheter interface 206c is shown in Detail G.

In Detail F, a third cooling chamber 210c is formed from a thermally conductive body. The chamber presents a small, closed cavity 234c. The small cavity in FIG. 12 is about 15 mm$^3$ to 60 mm$^3$, but smaller volumes and larger volumes are contemplated. As illustrated in FIG. 12, the thermally conductive body has a substantially cylindrical shape, but other shapes are possible. For example, if the cooling chamber 210c is configured for use adjacent to the basal or middle turns of a cochlear bone, the cooling chamber 210c may be formed with a flattened side, one or more valleys, one or more protuberances, or with other features formed to shapedly cooperate with a particular anatomical feature in a human patient.

The third cooling chamber 210c includes a plurality of orifices into the small, closed cavity 234c. A first orifice is coupled to a first lumen 228c of the multiport catheter 208c, a second orifice is coupled to a second lumen 230c of the multiport catheter 208c, and a third orifice is coupled to a third lumen 232c of the multiport catheter 208c. The second lumen 230c is coupled to the vent port of the third tubing manifold/catheter interface 206c.

A cross-hatch pattern on the surface of the third cooling chamber 210c indicates the presence of a biocompatible surface to the third cooling chamber 210. The biocompatible surface may be attributed to the material used to form the third cooling chamber 210. Alternatively, or in addition, the biocompatible surface may be attributed to a biocompatible agent.

The first lumen 228c of the third cooling chamber 210c passes fluid into the small cavity 234c, and the third lumen passes fluid out from the small cavity 234c of the third cooling chamber 210c. A filling tube 236c is friction fit into the third orifice. The filling tube 236c is arranged to mitigate bubble formation in the small, closed cavity 234c by off-setting the entry and exit points of a heat-transporting fluid.

In Detail F, an assembly joint 216c is formed as a cylinder, or sleeve. The assembly joint 216c has an inside profile only slightly larger than the outside profile of the third cooling chamber 210c and the third multiport catheter 208c. A certain adhesive sealant 218c, for example a biocompatible, flexible, wicking epoxy or glue forms a hermetic seal between the assembly joint 216c, the third cooling chamber 210c, and the third multiport catheter 208c. In some embodiments, the assembly joint is flexible, which may facilitate assembly, particularly if the third cooling chamber 210c and the third multiport catheter 208c have different cross-sectional profiles. In some cases, the adhesive sealant 218c forms a fixed bond between the enjoined components; in other cases, the bond is sealed, but separable with a determined opposing pressure applied to the third cooling chamber 210c and the third multiport catheter 208c.

Detail G of FIG. 12 illustrates a cross section of a portion of the third tubing manifold/catheter interface 206c. In particular, a non-limiting vent port embodiment is illustrated. As indicated in Detail G by a dashed line and arrow, a lumen in the third tubing manifold/catheter interface 206c is aligned with the third lumen 230c of the multiport catheter 208c. The third lumen 230c is arranged and assembled to pass air caught in the small cavity 234c out of the third cooling chamber 210c. A fluid lumen 246c in the third tubing manifold/catheter interface 206c passes fluid from the third lumen 232c of the multiport catheter 208c.

A venting lumen 238c communicates with the third lumen 230c of the multiport catheter 208c. The venting lumen 238c includes a dead-end channel 240c that can operate as an air gap. Air or other non-thermally conductive material removed from the small cavity 234c passes through the venting lumen 238c. A check valve 242c permits the air or other material to pass from the venting lumen 238c to the outside atmosphere. As illustrated in Detail G, the check valve 242c is a gravity and reverse pressure device, but other types of valves could also be used. In some cases, an active valve with suction is used.

A hydrophobic plug 244c terminates the venting lumen 238c. The hydrophobic plug 244c permits air or other gases to pass from the venting lumen while restricting the flow of liquid. In some cases, the hydrophobic plug 244c is formed from a polytetrafluoroethylene (PTFE) material, but other materials could also be used.

Figure 13:
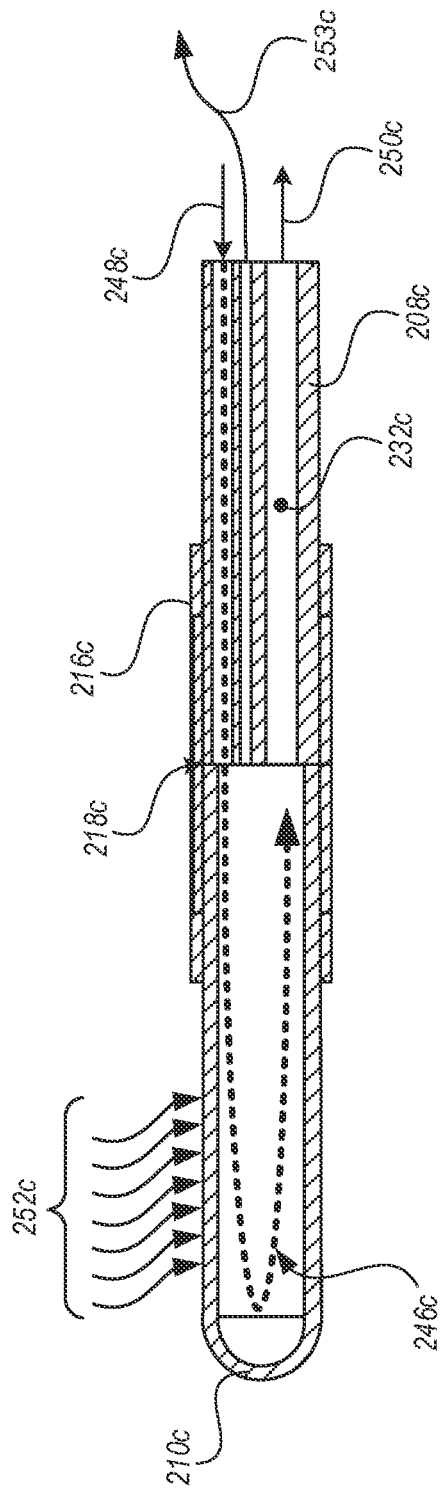
FIG. 13 illustrates the Detail F portion of the medical device embodiment of FIG. 12.

FIG. 13 illustrates the Detail F portion of the medical device embodiment of FIG. 12. A cross-section of the third cooling chamber 210c is shown along with the multiport catheter 208c joined to the third cooling chamber 210c by assembly joint 216c and adhesive sealant 218c.

In FIG. 13, a flow of heat-transporting fluid is shown by a dashed line 246c. The fluid passes into the medical device at 248c and out from the medical device at 250c. A heat graphic 252c indicates that heat drawn from the area proximate to the third cooling chamber 210c is absorbed through the wall of the third cooling chamber 210c by the heat-transporting fluid flowing in the small, closed cavity. Air flow 253c through the third lumen 230c of the multiport catheter 208c is also shown.

Figure 14:
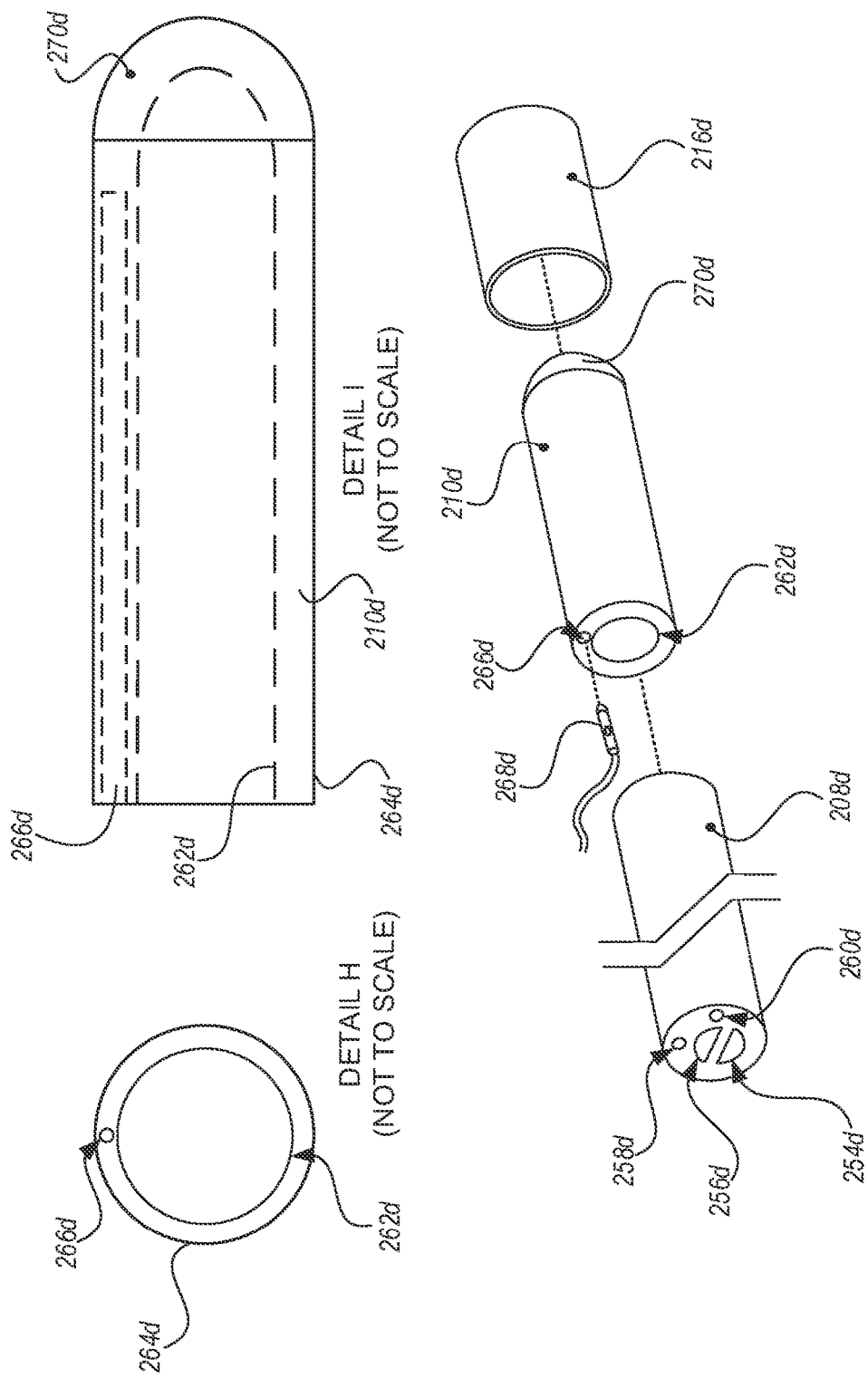
FIG. 14 illustrates exploded and detailed views of yet another medical device embodiment.

FIG. 14 illustrates exploded and detailed views of yet another medical device embodiment. The medical device of FIG. 14 includes a fourth cooling chamber 210d embodiment and a fourth multiport catheter 208d, coupleable with an assembly joint sleeve 216d. The fourth multiport catheter 208d is illustrated with four lumens, though a different number could also be formed. The particular shapes, position, and dimensions of the lumens in the multiport catheter 208d are non-limiting. In the fourth multiport catheter 208d, first and second lumens 254d, 256d are configured, respectively, to pass a heat-transporting fluid into and out from the fourth cooling chamber 210d. A third lumen 258d is configured to pass one or more electrically conductive wires. A fourth lumen 260d is a vent lumen to remove air or other thermally inefficient material from the fourth cooling chamber 210d.

A cross-section of the fourth cooling chamber 210d is illustrated in Detail "H." In the embodiment of FIG. 14, the fourth cooling chamber 210d is substantially cylindrical and substantially formed of a metal, such as copper, platinum, gold, or aluminum. The embodiment of the fourth cooling chamber 210d is exemplary, and formed having a 3.00 mm outside diameter (OD), a 2.03 mm inside diameter (ID), and a 6.00 mm length. Other embodiments of cooling chambers have very thin walls, for example 2.20 mm OD, 2.03 mm ID, and 3.00 mm length. Still other embodiments have different dimensions.

As shown in the cross section of the fourth cooling chamber 210d, an electric wire lumen 266d is formed between the inside wall 262d and the outside wall 264d of the fourth cooling chamber 210d. The electric wire lumen 266d is also shown in the hidden structure view of the fourth cooling chamber 210d of Detail "I." The electric wire lumen 266d is configured to receive an optional thermocouple/resistance temperature detector (RTD) device 268d.

In some cases, the fourth cooling chamber 210d is formed as a closed ended cylinder. In other cases, the fourth cooling chamber 210d is assembled with a machined end cap, which may be threaded and screwed on, welded, or joined in another way. In still other cases, for example as illustrated in FIG. 14, the end of the fourth cooling chamber 210d is formed with an epoxy seal 270d. The epoxy seal may include thermally conductive properties.

Figure 15:
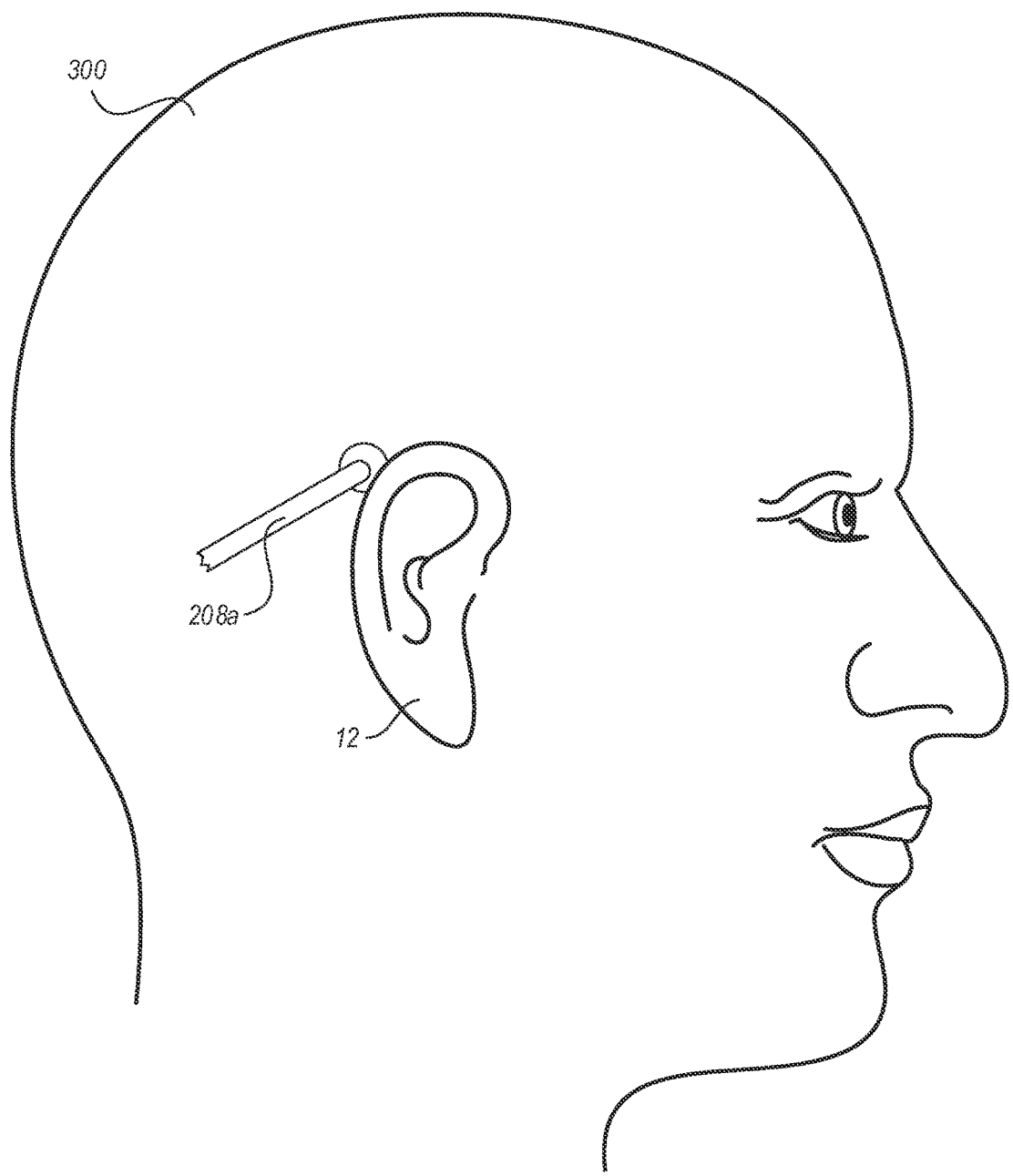
FIG. 15 illustrates a patient 300 undergoing a medical procedure.

FIG. 15 illustrates a patient 300 undergoing a medical procedure. A medical practitioner has cut a hole into the patient's skull behind the right ear 12. Through the hole, the medical practitioner will implant a cochlear electrode array into the patient's cochlea. In the medical procedure, a localized therapeutic hypothermia system 100 is being used to provide a therapeutic cooling effect to the anatomical structures of the patient's inner ear. Protruding from the skull, a first multi-lumen catheter 208a is observed. Other components of the localized therapeutic hypothermia system 100 are not shown for simplicity.

Figure 16:
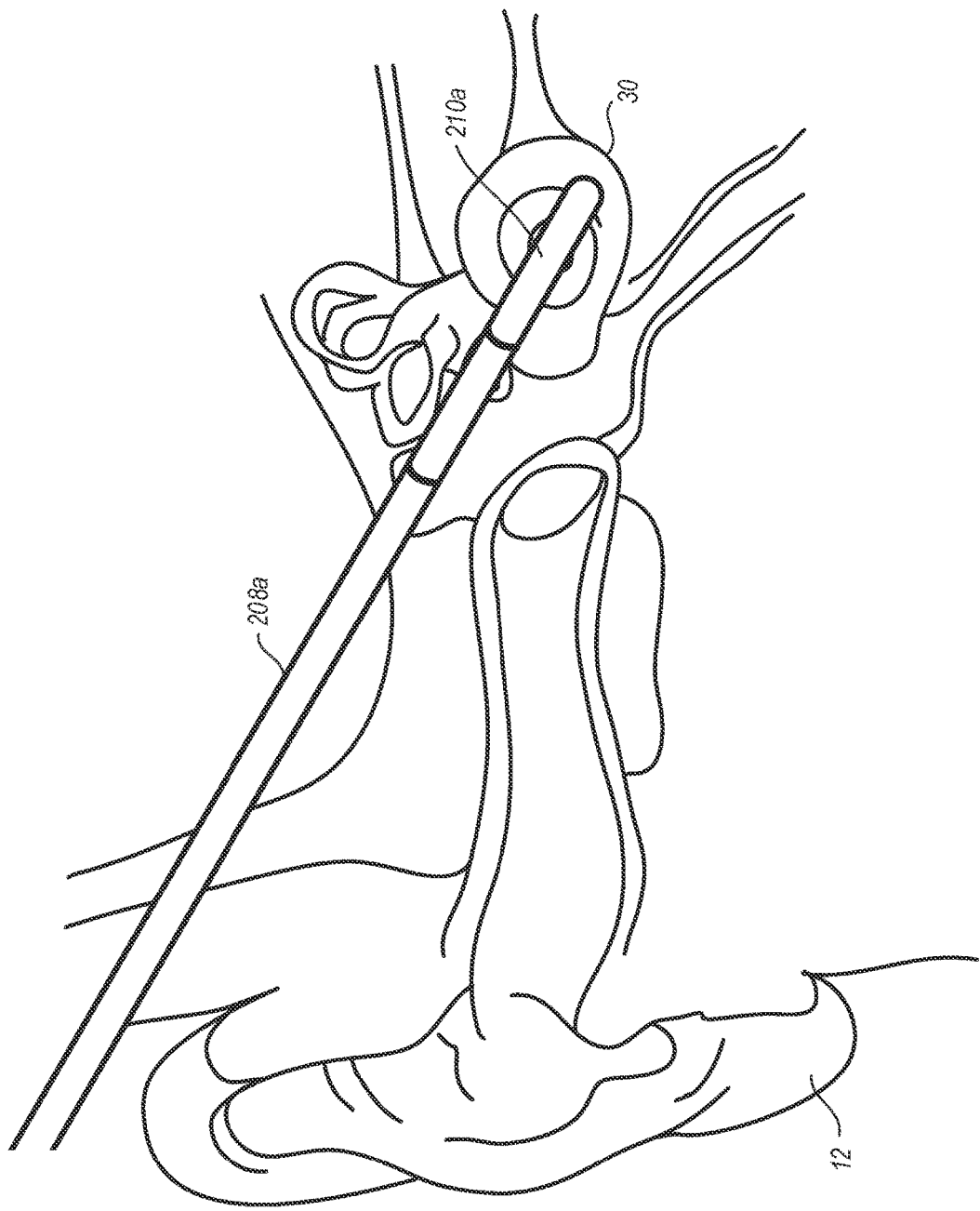
FIG. 16 illustrates a cut-away view of the patient 300 undergoing the medical procedure of FIG. 15.

FIG. 16 illustrates a cut-away view of the patient 300 undergoing the medical procedure of FIG. 15. In FIG. 16, the first cooling chamber 210a of the localized therapeutic hypothermia system 100 is applied to an area adjacent to the basal and middle turns of the patient's cochlea 30. During the cochlear implant surgery illustrated in FIG. 16, the first cooling chamber 210a is applied for about 15 to 30 minutes before the cochlear electrode array is introduced into the patient's cochlea. In some cases, the first cooling chamber 210*a* is maintained in a relatively stable proximity to the cochlea during the placement of the array. In some cases, the first cooling chamber 210*a* is maintained after the array placement for an additional 15 to 30 minutes. In the medical procedure of FIGS. 15 and 16, the cooling effect to the anatomical structures of the inner ear may be two (2) to six (6) degrees Celsius. Other temperature reductions may also be achieved.

Figure 17:
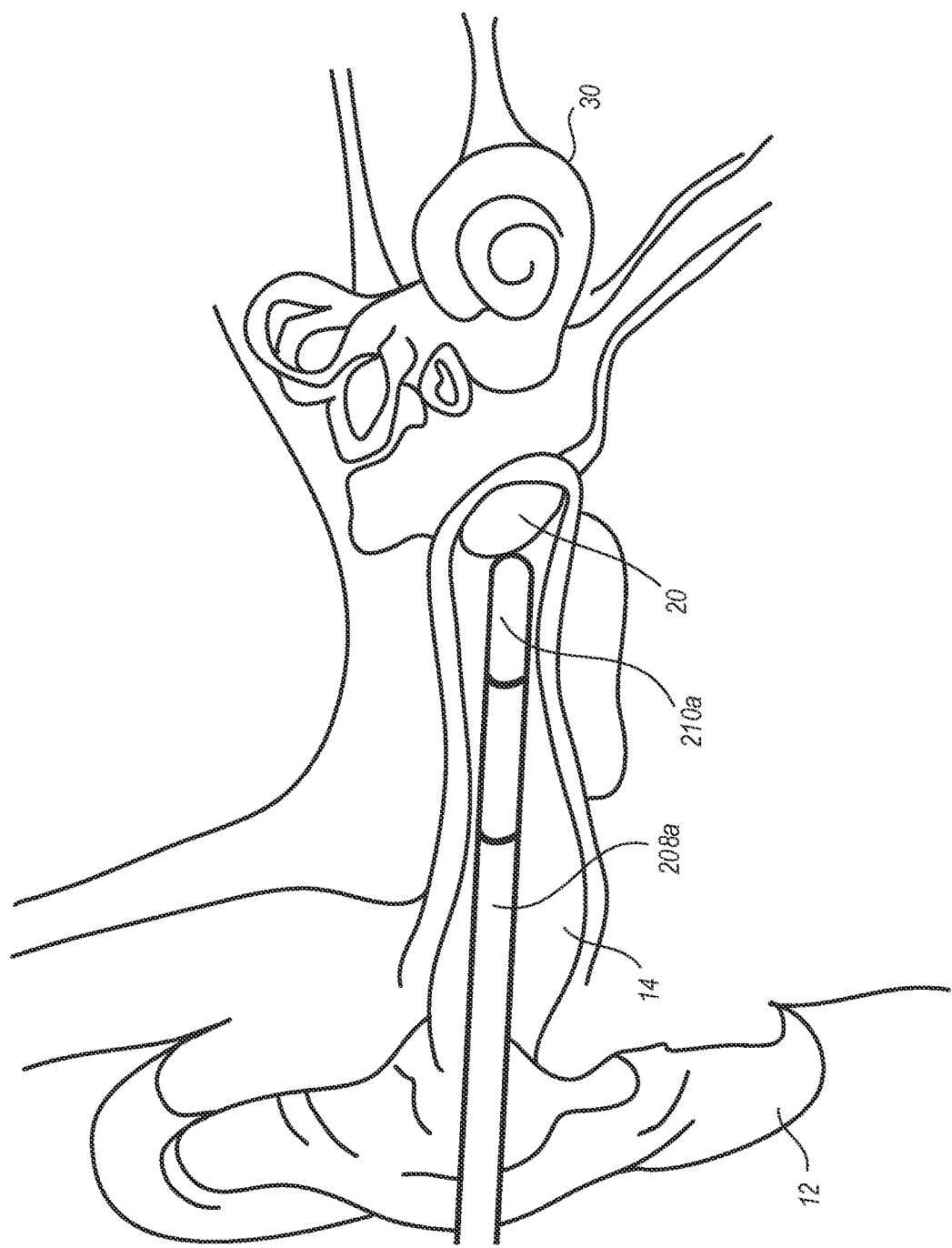
FIG. 17 illustrates a different use of the localized therapeutic hypothermia system in a medical procedure to the ear of a patient.

FIG. 17 illustrates a different use of the localized therapeutic hypothermia system 100 (FIG. 7) in a medical procedure to the ear of a patient 300. In FIG. 17, a portion of cooling tip 200*a*, and in particular, the first cooling chamber 210*a* and the first multi-lumen catheter 208*a*, are inserted into the external auditory canal 14. The first cooling chamber 210*a* is placed in proximity to the tympanic membrane (eardrum) 20, and the cooling effect in the cochlea 30 from the localized therapeutic hypothermia system 100 is achieved over a longer period of time, from a further distance away.

The procedure illustrated in FIG. 17 may be performed in a medical or non-medical environment. The procedure illustrated in FIG. 17 may be used to treat trauma to the middle and inner ear attributable to any source. For example, the procedure may treat middle and inner ear damage caused by surgery, infection, chemotherapy, intrusion of a physical device, other trauma of the head and neck (e.g., whiplash, concussion, and the like), a rapid pressure change, NIHL from blasts, loud music, or other acoustic and non-acoustic sources. Beneficial and effective therapeutic hypothermia using the devices and methods described herein can be applied prior to trauma, immediately following trauma, and at various times within the first 48 hours after trauma.

In some cases, the therapeutic hypothermia system 100 applied in FIG. 17 is a portable device. The portable device has a size and configuration conducive to deployment on a battlefield or at an accident site. Accordingly, the therapeutic hypothermia system 100 can be powered with a portable source (e.g., battery, solar cell, and the like). The therapeutic hypothermia system 100 can also be packaged in a small, sturdy case for easy transport in a medical kit, ambulance, and the like.

The cooling tip 200*a* of the therapeutic hypothermia system 100 illustrated in FIG. 17 may be shaped for a particular purpose. For example, the shape of the cooling tip 200*a* may be substantially cylindrical, substantially flat, or contours that mirror (i.e., mate) with a particular bone, organ, muscle, or some other biological matter. The shape of the cooling tip 200*a* may be based on an expected surface area and shape of an area to be cooled.

For protection against or prevention of NIHL using the approach illustrated in FIG. 17, the probe (i.e., a portion of the first multi-lumen catheter 208*a* and first cooling chamber 210*a* with cooling tip 200*a*) is placed in the external auditory/ear canal. The therapeutic hypothermia system 100 provides therapeutic cooling of the sensory cochlea and vestibular organs. In this embodiment, the therapeutic hypothermia may be used, inclusively or alternatively, before, during and after exposure to trauma that may damage sensitive vestibular organs.

Figure 18:
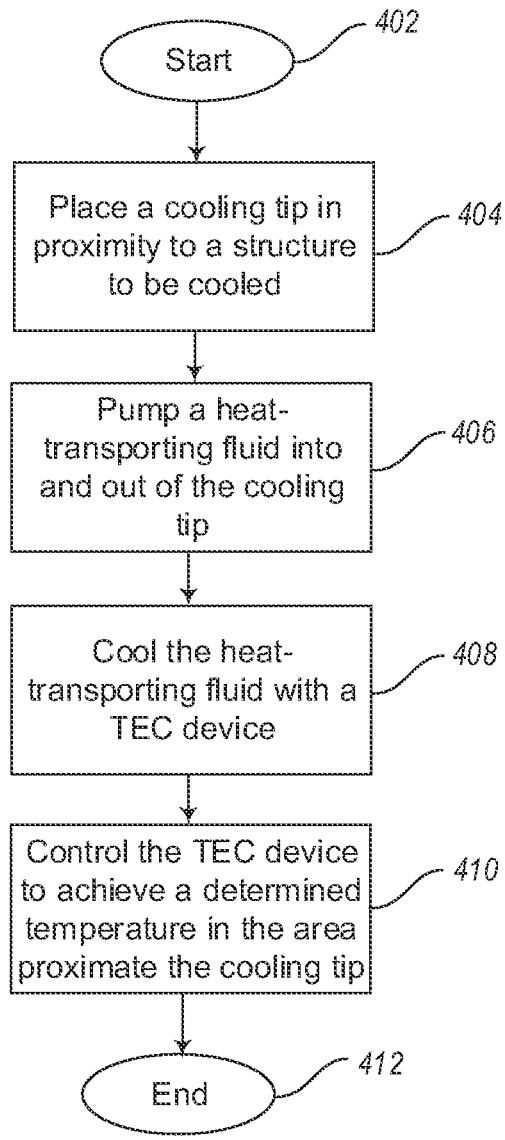
FIG. 18 includes a data flow diagram illustrating a non-limiting process that may be used by embodiments of a localized therapeutic hypothermia system.

FIG. 18 illustrates a method to provide localized therapeutic hypothermia 400. The method may be employed during a medical procedure such as a cochlear implant or in the treatment of other middle and inner ear trauma. The method begins at 402, and in a first act at 404, a cooling tip with a cavity of less than 60 mm$^3$ is placed in proximity to a structure to be cooled. The cavity in the cooling tip is formed within a body having thermo-conductive properties. A heat-transporting fluid is pumped into and out from the cooling tip at 406, and the heat-transporting fluid is cooled with a thermoelectric cooling device at 408. At 410, the thermoelectric cooling device is controlled to achieve a determined temperature in the area proximate the cooling tip. Processing ends at 412.

The method to provide localized therapeutic hypothermia 400 can be carried out using the embodiments described herein with respect to FIGS. 7-17, and many variations and additional acts are contemplated. For example, in some embodiments, the heat-transporting fluid is passed through a multiport catheter or through independent flexible tubing. In some embodiments, the closed system that contains the heat-transporting fluid is primed, which may also include opening a vent. The temperature in some systems that provide localized therapeutic hypothermia is sensed at the cooling tip, and in additional or alternative embodiments, temperature is sensed at or near the TEC. The TEC, which can be formed with a Peltier cooler, may be controlled by controlling voltage or current passing to the TEC. Other embodiments are also considered.

The devices and methods described herein induce localized hypothermia in small cavities and on surfaces where neuroprotective, function-protective qualities are desired. The device may be used by a wide variety of medical practitioners including surgeons, technicians, nurses or biomedical engineers assisting in surgery, first responders, and others. Potential applications of the present device and methods include use during surgeries intended to treat hearing loss associated with Traumatic Brain Injury (TBI), during Cochlear Implant surgery, during vestibular surgeries including surgical-occlusion/canal-plugging, nerve section surgery, other common head and neck surgeries where surgical trauma may lead to neural degeneration and functional loss. In addition, the application of localized hypothermia with devices described herein can be applied in acute or chronic hearing loss and balance/dizziness issues associated with blast, traumatic brain injuries (TBIs), head injury, accidents, chemotherapy, noise exposure, and administration of ototoxic drugs. The devices may also be used to provide benefits in many other medical procedures such as orthopedic surgeries such as knee/hip surgeries, skin surgeries, dental surgeries, and other surgeries to reduce inflammatory response and provide improved functional recovery.

Devices described herein have been reduced to practice. Using such devices, Auditory Brainstem Responses (ABRs) were performed to assess hearing function before and after cochlear implant surgeries. Surgeries were performed on one ear while providing localized mild hypothermia to the middle turn of the cochlea for 30 minutes before and after induction of trauma caused by the cochlear implant procedure. The hearing thresholds were compared to controls that did not receive hypothermia during surgery. In all cases the contralateral ear was used as an internal control. In acute experiments, ABRs were performed before surgery and at 30-minute intervals after surgery for 150 minutes. In the chronic experiments, ABRs were performed before surgery and at various time points up to 30 days after surgery.

In control ears that did not receive hypothermia during cochlear implantation, initial hearing threshold loss of 40 dB on average was observed. With the hypothermia device, about three (3) degrees Celsius cooling was observed from measurements taken at the round window in the inner ear. Hearing thresholds from the cochlea that received local hypothermia during cochlear implantation were similar to contralateral naive cochlea after initial insult. In chronic experiments, an initial hearing loss of average 51 dB at 16 kHz in the trauma only group was observed. Functional improvement in implanted cochlea that received hypothermia a few days after implantation surgery was observed. More specifically, the function of cochlea receiving therapeutic hypothermia was conserved with an elevation on average of 8 dB and hearing thresholds returned to pre-surgical levels rapidly.

Histology has shown cilia (hair cell) loss in the basal turn of the cochlea caused by implantation surgery corresponds to hearing loss caused by surgical trauma due to other procedures. Observed results show that mild localized hypothermia prevented significant functional loss due to damage caused by the cochlear implant surgery.

In the embodiments of present disclosure, a particular fluid flows in a closed system. The various components and devices of the embodiments are interchangeably described herein as "coupled," "connected," "attached," and the like. It is recognized that once assembled, the system is hermetically sealed to prevent the fluid from escaping the system. The materials and the junctions formed at the point where two or more structures meet in the present embodiments are sealed to a medically or otherwise industrially acceptable level.

Furthermore, in the present disclosure, catheters are described as having one or more lumens. A lumen, which may be thought of as a cavity or passage in a tubular structure, may also be interchangeably identified herein as a port, tube, or other similar void as the circumstances may provide.

FIG. 18 includes a data flow diagram illustrating a non-limiting process that may be used by embodiments of a localized therapeutic hypothermia system 100. In this regard, each described process may represent a module, segment, or portion of software code, which comprises one or more executable instructions for implementing the specified logical function(s). It should also be noted that in some implementations, the functions noted in the process may occur in a different order, may include additional functions, may occur concurrently, and/or may be omitted.

The figures in the present disclosure illustrate portions of one or more non-limiting computing device embodiments such as control system 102. The computing devices may include operative hardware found in conventional computing device apparatuses such as one or more processors, volatile and non-volatile memory, serial and parallel input/output (I/O) circuitry compliant with various standards and protocols, wired and/or wireless networking circuitry (e.g., a communications transceiver), one or more user interface (UI) modules, logic, and other electronic circuitry.

Processors, as described herein, include central processing units (CPU's), microcontrollers (MCU), digital signal processors (DSP), application specific integrated circuits (ASIC), and the like. The processors interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, embodiments describe software executable by the processor and operable to execute certain ones of the method acts.

As known by one skilled in the art, a computing device has one or more memories, and each memory comprises any combination of volatile and non-volatile computer-readable media for reading and writing. Volatile computer-readable media includes, for example, random access memory (RAM). Non-volatile computer-readable media includes, for example, read only memory (ROM), magnetic media such as a hard-disk, an optical disk drive, a floppy diskette, a flash memory device, a CD-ROM, and/or the like. In some cases, a particular memory is separated virtually or physically into separate areas, such as a first memory, a second memory, a third memory, etc. In these cases, it is understood that the different divisions of memory may be in different devices or embodied in a single memory. The memory in some cases is a non-transitory computer medium configured to store software instructions arranged to be executed by a processor.

The computing devices illustrated herein may further include operative software found in a conventional computing device such as an operating system or task loop, software drivers to direct operations through I/O circuitry, networking circuitry, and other peripheral component circuitry. In addition, the computing devices may include operative application software such as network software for communicating with other computing devices, database software for building and maintaining databases, and task management software where appropriate for distributing the communication and/or operational workload amongst various processors. In some cases, the computing device is a single hardware machine having at least some of the hardware and software listed herein, and in other cases, the computing device is a networked collection of hardware and software machines working together in a server farm to execute the functions of one or more embodiments described herein. Some aspects of the conventional hardware and software of the computing device are not shown in the figures for simplicity.

When so arranged as described herein, each computing device may be transformed from a generic and unspecific computing device to a combination device comprising hardware and software configured for a specific and particular purpose.

Database structures, if any are present in the localized therapeutic hypothermia system 100, may be formed in a single database or multiple databases. In some cases hardware or software storage repositories are shared amongst various functions of the particular system or systems to which they are associated. A database may be formed as part of a local system or local area network. Alternatively, or in addition, a database may be formed remotely, such as within a "cloud" computing system, which would be accessible via a wide area network or some other network.

Input/output (I/O) circuitry and user interface (UI) modules include serial ports, parallel ports, universal serial bus (USB) ports, IEEE 802.11 transceivers and other transceivers compliant with protocols administered by one or more standard-setting bodies, displays, projectors, printers, keyboards, computer mice, microphones, micro-electro-mechanical (MEMS) devices such as accelerometers, and the like.

In at least one embodiment, devices such as the control system 102 may communicate with other devices via communication over a network. The network may involve an Internet connection or some other type of local area network (LAN) or wide area network (WAN). Non-limiting examples of structures that enable or form parts of a network include, but are not limited to, an Ethernet, twisted pair Ethernet, digital subscriber loop (DSL) devices, wireless LAN, WiFi, Worldwide Interoperability for Microwave Access (WiMax), or the like.

In some cases, the memory 104 is a non-transitory computer readable medium (CRM). The CRM is configured to store computing instructions executable by a CPU of the control system 102. The computing instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of a localized therapeutic hypothermia system 100.

Buttons, keypads, computer mice, memory cards, serial ports, bio-sensor readers, touch screens, and the like may individually or in cooperation be useful to an operator of the localized therapeutic hypothermia system 100. The devices may, for example, input control information into the system. Displays, printers, memory cards, LED indicators, temperature sensors, audio devices (e.g., speakers, piezo device, etc.), vibrators, and the like are all useful to present output information to the operator of the localized therapeutic hypothermia system 100. In some cases, the input and output devices are directly coupled to the control system 102 and electronically coupled to a CPU or other operative circuitry. In other cases, the input and output devices pass information via one or more communication ports (e.g., RS-232, RS-485, infrared, USB, etc.)

As described herein, for simplicity, a medical practitioner may in some cases be described in the context of the male gender. It is understood that a medical practitioner can be of any gender, and the terms "he," "his," and the like as used herein are to be interpreted broadly inclusive of all known gender definitions.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, the technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

In the foregoing description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks, have not been shown or described in detail to avoid unnecessarily obscuring descriptions of the embodiments.

Unless the context requires otherwise, throughout the specification and claims which follow, the word "comprise" and variations thereof, such as "comprises" and "comprising" are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A medical device to locally cool a cochlear region, comprising:

a thermally conductive cooling tip having a reservoir formed therein, the reservoir having an entry point for heat-transporting fluid and an exit point for the heat-transporting fluid;

a multiport catheter coupled to the thermally conductive cooling tip, the multiport catheter having a first lumen, a second lumen, and a third lumen arranged in a closed system that contains the heat-transporting fluid, the first lumen arranged to pass the heat-transporting fluid in a first direction toward the thermally conductive cooling tip, the second lumen arranged to pass the heat-transporting fluid in a second direction away from the thermally conductive cooling tip, wherein the first lumen has a larger cross-sectional area than the second lumen to create a pressure differential in the closed system that forces the reservoir to be completely and persistently filled with the heat-transporting fluid when the closed system is under pressure, and wherein the third lumen is arranged as a filling tube friction fit into the first lumen or the second lumen to mitigate bubble formation in the thermally conductive cooling tip reservoir by offsetting the entry and exit points of the heat-transporting fluid;

a pump having an output port and an input port, the output port coupled to the first lumen, the input port coupled to the second lumen, the pump configured to create pressure in the closed system that will move the heat-transporting fluid from the output port toward the reservoir at a first pressure and from the reservoir toward the input port at a second different pressure; and a thermoelectric cooling system, the thermoelectric cooling system having a cooling side and an opposite side, the cooling side assembled in proximity to a portion of the multiport catheter.

2. The medical device of claim 1, further comprising:
a control module, the control module configured to control at least one parameter affecting a hysteresis function of the thermoelectric cooling system.

3. The medical device of claim 2, further comprising:
at least one temperature responsive element coupled to the control module.

4. The medical device of claim 2, further comprising:
a user interface coupled to the control module, the user interface arranged to accept at least one input parameter associated with a temperature of the thermally conductive cooling tip, the user interface arranged to present at least one status output.

5. The medical device of claim 1, wherein the thermally conductive cooling tip is arranged with at one or more valleys and one or more protuberances to shapedly cooperate with a cochlear bone.

6. The medical device of claim 1, further comprising:
a flexible assembly joint arranged on an outer surface of the thermally conductive cooling tip and an outer surface of the multiport catheter to couple the thermally conductive cooling tip to the multiport catheter, wherein the thermally conductive cooling tip and the multiport catheter have different cross-sectional profiles.

7. The medical device of claim 1, wherein the thermally conductive cooling tip is formed using at least one metal, and wherein the first and second lumens each have a semi-circular cross section.

8. The medical device of claim 1, wherein the multiport catheter and thermally conductive cooling tip are removable from the medical device, and the multiport catheter and thermally conductive cooling tip are sterilizable.

9. A medical device, comprising:
a multiport catheter including a plurality of lumens arranged to form a closed system having a heat-transporting fluid contained therein;
a thermally conductive cooling tip having a body with a substantially cylindrical shape, the body formed of a thermally conductive material, the body forming a closed cavity, the body having a first orifice coupled to a first lumen of the plurality of lumens of the multiport catheter, a second orifice coupled to a second lumen of the plurality of lumens of the multiport catheter, and a filling tube friction fit into the first lumen or the second lumen to mitigate bubble formation in the thermally conductive cooling tip by offsetting the first and second orifices, wherein a size difference between the first lumen and the second lumen creates a pressure differential in the closed system that forces the closed cavity to be completely and persistently filled with the heat-transporting fluid when the closed system is under pressure; and
a sealing structure joining the multiport catheter to the thermally conductive cooling tip.

10. The medical device of claim 9, further comprising:
a temperature responsive element integrated within the thermally conductive cooling tip.

11. The medical device of claim 9, wherein the multiport catheter comprises:

a third lumen, the third lumen being outside of the closed system and arranged to vent the multiport catheter via a one-way valve, wherein the heat-transporting fluid is a fluorocarbon.

12. The medical device of claim 9, wherein the thermally conductive cooling tip is shaped to mate with at least one structure of a vestibular system.

13. The medical device of claim 9, further comprising:
a thermoelectric cooling system coupled to the multiport catheter.

14. The medical device of claim 9, wherein an outer surface of the thermally conductive cooling tip includes a biocompatible material.

15. The medical device of claim 9, further comprising:
a peristaltic pump positioned proximal to the multiport catheter and arranged to pressurize the closed system when the peristaltic pump is operated.

16. A method to provide localized therapeutic hypothermia, comprising:
placing a cooling tip in proximity to a biological structure to be cooled, the cooling tip having thermo-conductive properties and an internal cavity formed therein, the cooling tip having a heat-transporting fluid supplied via filling tube friction fit into a first lumen and removed via a second lumen, the first and second lumens sized to create a pressure differential that completely and persistently fills the internal cavity with the heat-transporting fluid when the heat-transporting fluid is under pressure, the filling tube arranged to offset entry and exit points for the heat-transporting fluid to mitigate bubble formation in the cooling tip;
pumping the heat-transporting fluid into and out from the internal cavity of the cooling tip;
removing heat from the heat-transporting fluid with a thermoelectric cooling device; and
controlling the thermoelectric cooling device to achieve a determined temperature in an area proximate the cooling tip.

17. The method of claim 16, wherein the internal cavity of the cooling tip has a volume of about 60 mm$^3$ or less.

18. The method of claim 16, further comprising:
performing a medical procedure on the biological structure, the medical procedure causing trauma to the biological structure, wherein placing the cooling tip in proximity to the biological structure to be cooled includes placing the cooling tip in proximity to the biological structure between 15 and 30 minutes before the biological structure is traumatized by the medical procedure.

19. The method of claim 18, wherein placing the cooling tip in proximity to the biological structure to be cooled further includes placing the cooling tip in proximity to the biological structure between 15 and 30 minutes after the structure is traumatized.

20. The method of claim 18, wherein the medical procedure includes implantation of a cochlear device.

21. The method of claim 16, wherein placing the cooling tip in proximity to the biological structure to be cooled includes placing the cooling tip in proximity to the biological structure within 48 hours after the biological structure is traumatized.

* * * * *